(12) United States Patent
Ekwuribe et al.

(10) Patent No.: US 7,119,074 B2
(45) Date of Patent: Oct. 10, 2006

(54) TREATMENT OF CANCERS, TUMORS AND MALIGNANCIES USING AMPHIPHILIC PRODRUGS

(75) Inventors: Nnochiri Ekwuribe, Cary, NC (US); Christopher H. Price, Chapel Hill, NC (US); Tatyana A. Dyakonov, Greensboro, NC (US)

(73) Assignee: Nobex Corporation, Durham, NC (US)

( * ) Notice: Subject to any disclaimer, the term of this patent is extended or adjusted under 35 U.S.C. 154(b) by 30 days.

(21) Appl. No.: 10/808,044

(22) Filed: Mar. 24, 2004

(65) Prior Publication Data

US 2004/0180840 A1    Sep. 16, 2004

Related U.S. Application Data

(62) Division of application No. 09/474,915, filed on Dec. 31, 1999, now Pat. No. 6,713,454.

(60) Provisional application No. 60/153,649, filed on Sep. 13, 1999.

(51) Int. Cl.
*A61K 31/704* (2006.01)

(52) U.S. Cl. ........................ 514/25

(58) Field of Classification Search ........... 514/25
See application file for complete search history.

(56) References Cited

U.S. PATENT DOCUMENTS

| | | | |
|---|---|---|---|
| 4,567,253 A | 1/1986 | Durst et al. | 536/18.1 |
| 4,636,505 A | 1/1987 | Tucker | 514/256 |
| 5,122,614 A | 6/1992 | Zalipsky | 548/520 |
| 5,219,564 A | 6/1993 | Zalipsky et al. | 424/78.17 |
| 5,298,643 A | 3/1994 | Greenwald | 558/6 |
| 5,321,095 A | 6/1994 | Greenwald | 525/404 |
| 5,324,844 A | 6/1994 | Zalipsky | 548/520 |
| 5,349,001 A | 9/1994 | Greenwald et al. | 525/408 |
| 5,405,877 A | 4/1995 | Greenwald et al. | 514/772.3 |
| 5,407,683 A | 4/1995 | Shively | 424/439 |
| 5,422,364 A | 6/1995 | Nicolaou et al. | 514/449 |
| 5,439,686 A | 8/1995 | Desai et al. | 424/451 |
| 5,455,027 A | 10/1995 | Zalipsky et al. | 424/78.17 |
| 5,484,809 A | 1/1996 | Hostetler et al. | 514/449 |
| 5,547,981 A | 8/1996 | Greenwald et al. | 514/449 |
| 5,560,933 A | 10/1996 | Soon-Shiong et al. | 424/489 |
| 5,567,422 A | 10/1996 | Greenwald | 424/78.3 |
| 5,605,976 A | 2/1997 | Martinez et al. | 525/408 |
| 5,608,087 A | 3/1997 | Nicolaou et al. | 549/510 |
| 5,612,460 A | 3/1997 | Zalipsky | 530/391.9 |
| 5,614,549 A | 3/1997 | Greenwald et al. | 514/449 |
| 5,618,528 A | 4/1997 | Cooper et al. | 424/78.3 |
| 5,622,986 A | 4/1997 | Greenwald et al. | 514/449 |

(Continued)

FOREIGN PATENT DOCUMENTS

EP    0 423 747 B1    10/1990

(Continued)

OTHER PUBLICATIONS

Greenwald et al., "Drug Delivery of Anticancer Agents: Water Soluble 4-Poly (Ethylene Glycol) Derivatives of the Lignan, Podophyllotoxin," *Journal of Controlled Release*, 61:281-294 (1999).

International Search Report corresponding to International Application No. PCT/US 00/24520; Date of mailing: Jul. 31, 2001.

(Continued)

*Primary Examiner*—Leigh C. Maier
(74) *Attorney, Agent, or Firm*—William A. Barrett; Moore & Van Allen PLLC

(57) ABSTRACT

The present invention provides amphiphilic prodrugs comprising a therapeutic compound conjugated to an PEG-oligomer/polymer and methods for using said prodrugs to enable oral drug delivery and/or delivery of drugs across the blood brain barrier into the central nervous system.

34 Claims, 6 Drawing Sheets

U.S. PATENT DOCUMENTS

Figure 1:
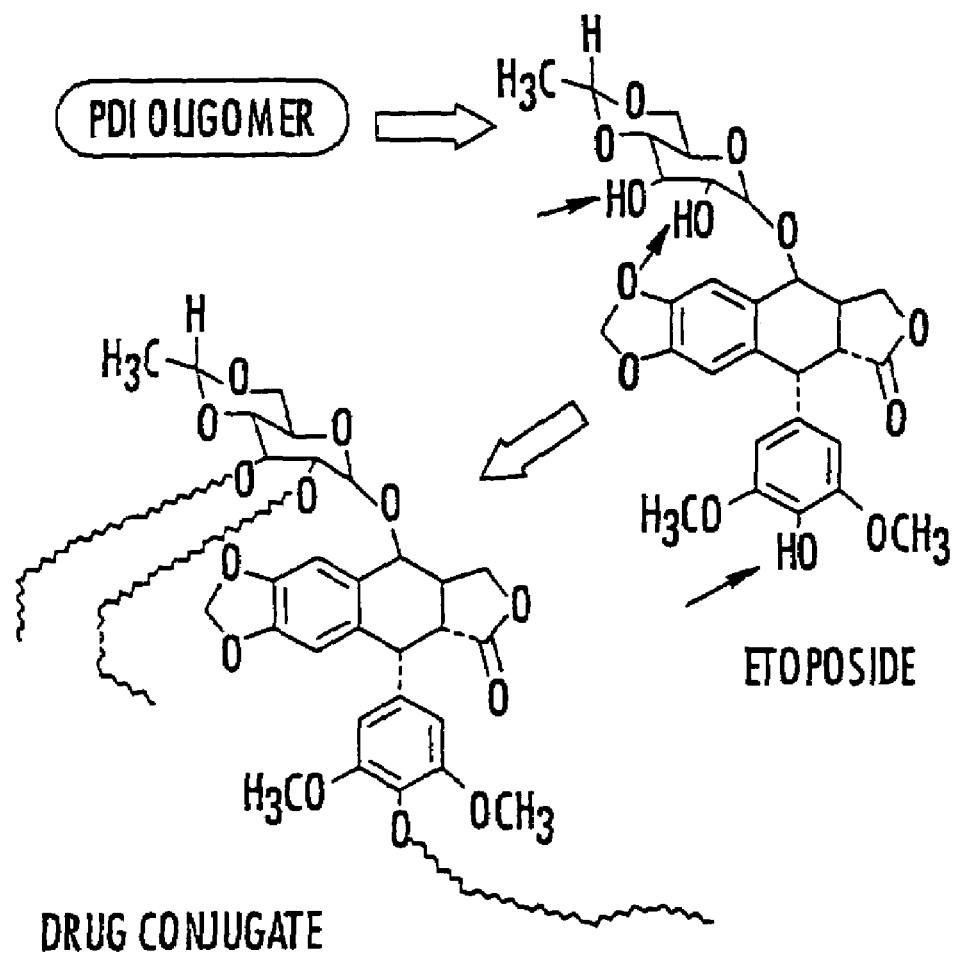

| | | | |
|---|---|---|---|
| 5,637,749 A | 6/1997 | Greenwald | 558/6 |
| 5,643,575 A | 7/1997 | Martinez et al. | 424/194.1 |
| 5,681,567 A | 10/1997 | Martinez et al. | 424/178.1 |
| 5,681,811 A | 10/1997 | Ekwuribe | 514/8 |
| 5,730,990 A | 3/1998 | Greenwald et al. | 424/279.1 |
| 5,744,592 A | 4/1998 | Hostetler et al. | 536/22.1 |
| 5,756,593 A | 5/1998 | Martinez et al. | 525/403 |
| 5,795,909 A | 8/1998 | Shashoua et al. | 514/449 |
| 5,808,096 A | 9/1998 | Zalipsky | 548/520 |
| 5,817,321 A | 10/1998 | Alakhov et al. | 424/400 |
| 5,817,840 A | 10/1998 | Nicolaou et al. | 549/510 |
| 5,824,701 A | 10/1998 | Greenwald et al. | 514/449 |
| 5,840,900 A | 11/1998 | Greenwald et al. | 546/48 |
| 5,880,131 A | 3/1999 | Greenwald et al. | 514/279 |
| 5,902,588 A | 5/1999 | Greenwald et al. | 424/278.1 |
| 5,919,455 A | 7/1999 | Greenwald et al. | 424/178.1 |
| 5,932,462 A | 8/1999 | Harris et al. | 435/188 |
| 5,965,119 A | 10/1999 | Greenwald et al. | 424/78.37 |
| 5,965,566 A | 10/1999 | Greenwald et al. | 514/279 |
| 6,011,042 A | 1/2000 | Greenwald et al. | 514/283 |
| 6,111,107 A | 8/2000 | Greenwald et al. | 546/48 |
| 6,113,906 A | 9/2000 | Greenwald et al. | 424/194.1 |
| 6,127,355 A | 10/2000 | Greenwald et al. | 514/183 |
| 6,153,655 A | 11/2000 | Martinez et al. | 514/772.3 |
| 6,177,087 B1 | 1/2001 | Greenwald et al. | 424/278.1 |
| 6,180,095 B1 | 1/2001 | Greenwald et al. | 424/85.1 |
| 6,194,580 B1 | 2/2001 | Greenwald et al. | 546/48 |
| 6,309,633 B1 | 10/2001 | Ekwuribe | 424/85.1 |
| 6,310,039 B1 | 10/2001 | Kratz | 514/8 |
| 6,380,405 B1 | 4/2002 | Ekwuribe | 549/510 |
| 6,541,508 B1 | 4/2003 | Ekwuribe | 514/449 |
| 6,703,381 B1 | 3/2004 | Ekwuribe | 514/182 |
| 6,713,454 B1 | 3/2004 | Ekwuribe | 514/25 |

FOREIGN PATENT DOCUMENTS

| | | |
|---|---|---|
| EP | 0 895 784 A1 | 2/1999 |
| HU | P9600612 A | 9/1996 |
| JP | 07082291 | 3/1995 |
| WO | WO93/24476 | 12/1993 |
| WO | WO 94/04484 | 3/1994 |
| WO | WO 94/12463 | 6/1994 |
| WO | WO94/20453 | 9/1994 |
| WO | WO 96/23794 | 8/1996 |
| WO | WO 97/33552 | 9/1997 |
| WO | WO 98/07713 | 2/1998 |
| WO | WO 98/10651 | 3/1998 |
| WO | WO 98/58927 | 12/1998 |
| WO | WO 99/30727 | 6/1999 |
| WO | WO99/48536 | 9/1999 |
| WO | WO 00/09073 | 2/2000 |
| WO | WO 00/64486 | 11/2000 |
| WO | WO 00/78302 | 12/2000 |
| WO | WO01/13957 | 3/2001 |
| WO | WO 01/19406 | 3/2001 |
| WO | WO 01/19407 | 3/2001 |

OTHER PUBLICATIONS

U.S. Appl. No. 60/153,649, entitled "Amphiphilic Prodrugs," filed Sep. 13, 1999.

U.S. Appl. No. 60/153,579, entitled "Taxane Prodrugs," filed Sep. 13, 1999.

U.S. Appl. No. 10/018,879, entitled "Amphiphilic Insulin-Oligomer Conjugates with Hydrolyzable Lipophile Components," filed Aug. 5, 2002.

International Search Report Corresponding to International Application No. PCT/US 00/24523; Date of Mailing: Aug. 6, 2001.

U.S. Appl. No. 10/774,903, entitled "Amphiphilic Drug-Oligomer Conjugates with Hydrolyzable Lipophile Components and Methods for Making and Using the Same" filed Feb. 9, 2004.

U.S. Appl. No. 10/811, 760, entitled "Drug-Oligomer Conjugates" filed Mar. 29, 2004.

U.S. Appl. No. 10/395,548, entitled "Taxane Prodrugs" filed Mar. 24, 2003.

U.S. Appl. No. 09/429,798, entitled "Blood-Brain Barrier Therapeutics" filed Oct. 29, 1999.

U.S. Appl. No. 09/430,735, entitled "Methods of Inducing Analgesia" filed Oct. 29, 1999.

U.S. Appl. No. 10/716,975, entitled "Methods of Activating Receptor Using Amphiphilic Drug-Oligomer Conjugates" filed Nov. 19, 2003.

U.S. Appl. No. 10/716,578, entitled "Methods of Altering the Binding Affinity of a Peptide to its Receptor" filed Nov. 11, 2003.

Adams, Jonathan D., et al. "Taxol: A History of Pharmaceutical Development and Current Pharmaceutical Concerns." J. Natl Cancer Inst Monographs (1993) 15: 141-147.

Arbuck, S.G. "Taxol (paclitaxel): Future directions." Annals of Oncology (1994) 5(Suppl 6): S59-S62.

Beijnen, Jos H., et al. "Bioanalysis, Pharmacokinetics, and Pharmacodynamics of the Novel Anticancer Drug Paclitaxel (Taxol)." Sem in Oncology (1994) 21 (5) (Suppl Oct. 8) 53-62.

Deutsch, H.M., et al. "Synthesis of Congeners and Prodrugs. 3.[1] Water-Soluble Prodrugs of Taxol with Potent Antitumor Activity." J Medicinal Chem (1989) 32: 788-792.

Greenwald, R.B., et al. "Drug Delivery Systems: Water Soluble Taxol 2'-Poly(ethylene) glycol) Ester Prodrugs—Design and in Vivo Effectiveness." J. Medicinal Chem (1996) 39:424-431.

Greenwald, R.B. et al. "Highly Water Soluble Taxol Derivatives: 7-Polyethylene Glycol Carbamates and Carbonates." J Org Chem (1995) 60: 331-336.

Horwitz, S.B. "TAXOL (paclitaxel): Mechanisms of action." Annals of Oncology (1994) 5 (Suppl.6): S3-S6.

Kingston, David G.I. "Taxol: the chemistry and structure-activity relationships of a novel anticancer agent." TIBTECH (Jun. 1994) 12: 222-227.

Kingston, David G.I. "The chemistry of Taxol." Pharmac Ther (1991) 52: 1-33.

Kohler, David R., et al. "Paclitaxel (Taxol)." (1994) Pharmacotherapy 14 (1): 3-34.

Long, Harry J. "Paclitaxel (Taxol): A Novel Anticancer Chemotherapeutic Drug." Mayo Clin Proc (1994) 69: 341-345.

Parekh, H. et al. "The Transport and Binding of Taxol." Gen Pharmac (1997) 29 (2): 167-172.

Preston, N.J. "Paclitaxel (Taxol)—a guide to administration." European J of Cancer Care (1996) 5: 147-152.

Rowinsky, Eric K. et al. "The Clinical Pharmacology and Use of Antimicrotubule Agents in Cancer Chemotherapeutics." Pharmac Ther (1991) 52: 35-84.

Rowinsky, Eric K. et al. "Taxol: The First of the Taxanes, an Important New Class of Antitumor Agents." Seminars in Oncology (Dec. 1992) 19(6): 646-662.

Rowinsky, Eric K. et al. "Taxol: Pharmacology, Metabolism and Clinical Implications." Cancer Surveys (1993) 17: 283-304.

Straubinger, Robert M. et al. "Novel Taxol Formulations: Taxol-Containing Liposomes." J Nat Cancer Inst Monographs (1993) No. 15: 69-78.

Workman, Paul. "Pharmacokinetics and Cancer: Successes, Failures and Future Prospects." Cancer Surveys (1993) 17: 1-26.

Delgado et al. "The Uses and Properties of PEG-Linked Proteins". *Critical Review in Therapeutic Drug Carrier Systems*, 9(3, 4):249-304 (1992).

Doyle et al. "Second generation analogs of etoposide and mitomycin C." *Cancer Treatment Reviews* (1990) 17, 127-131.

Abstract. Spigelman MK et al. "Effect of intracarotid etoposide on opening the blood-brain barrier." *Cancer Drug Deliv* 1984 Summer; 1(3):207-11.

Etoposide Conjugates Search in Chemical Abstracts File.

"Indications for Etoposide" http://www.medscape.com/FirstDataBank/cc . . . 20%20%20%20%20%20%20%20%&joc;_seqno=3930; Sep. 3, 1999.

Simon Joel "Antitumour Treatment; The Clinical Pharmacology of Etoposide: an update". *Cancer Treatment Reviews* (1996) 22, 179-221.

"Epipodophyllotoxins". Chapter 51 Antineoplastic Agents. 1261-1262.

Hungarian Novelty Search Report dated May 27, 2003 for Hungarian Patent Application No. P0204110.

Chabner et al., "Antineoplastic Agents: Epipodophyllotoxins," *Goodman & Gilman's The Pharmacological Basis of Therapeutics*, Ed. Hardman et al., Ninth Edition, Chapter 51, 1261-1262 (McGraw-Hill, 1996).

TREATMENT OF CANCERS, TUMORS AND MALIGNANCIES USING AMPHIPHILIC PRODRUGS

RELATED APPLICATIONS

This application is a divisional application of U.S. patent application Ser. No. 09/474,915, filed Dec. 31, 1999, issued on Mar. 30, 2004 as U.S. Pat. No. 6,713,454, which claims priority from U.S. Provisional Application No. 60/153,649, filed Sep. 13, 1999, the disclosures of which are incorporated herein by reference in their entireties.

1. BACKGROUND OF THE INVENTION

1.1 Field of the Invention

The present invention provides amphiphilic prodrugs comprising a therapeutic compound conjugated to an PEG-oligomer/polymer and methods for using said prodrugs to enable oral drug delivery and/or delivery of drugs across the blood brain barrier (BBB).

1.2 Related Art

The following is a discussion of art related to the present invention.

1.2.1 Cancer of the Central Nervous System (CNS)

The American Cancer Society estimates that 16,800 people will be diagnosed with primary tumors of the central nervous system (CNS) in the United States in 1999, and that 13,100 of these will eventually die of their disease (American Cancer Society, 1999). Primary CNS tumors are among the most intractable cancers to treat. While such tumors rarely metastasize, their anatomic location causes a high incidence of morbidity and mortality resulting from compression of surrounding tissue as well as destruction of tissue invaded by such tumors. Additionally, CNS tumor cells often migrate away from the tumor to other locations in the brain. These migratory cells eventually form recurrent tumors. Multiple CNS tumors can also result from metastases of non-CNS neoplasmas.

Standard treatment for CNS tumors includes surgery and radiation therapy. However, with regard to surgery, complete surgical resection is often not possible. Normal brain tissue adjacent to the tumor is often critical to the survival or the quality of life of the patient. Consequently, survival of patients treated by surgery is low. The problems associated with radiation therapy are widely known in the art.

Systemic chemotherapy, would be a valuable therapeutic option for CNS tumors due to its ability to target microscopic deposits of tumor cells, including cells missed by radiation and surgery. However, the inability to get such agents across the BBB has proven to be a significant limitation to the use of chemotherapy in the CNS. Many agents with activity against tumors do not cross the BBB to enter the brain parenchyma. Further, although many proven antineoplastic agents, including etoposide, will accumulate in brain tumors (Kiya, Uozumi et al. 1992), the concentration of these drugs decreases rapidly with distance from the tumor (Donelli, Zucchetti et al. 1992). In order to achieve effective treatment of the whole brain and expose microdeposits of tumor cells to drug, it would be desirable to have means for delivering therapeutic concentrations of anti-cancer drugs to the entire volume of the brain.

1.2.2 Barriers to CNS Drug Delivery

The brain is equipped with a barrier system which must be traversed to permit therapeutic drug delivery to the CNS. This brain barrier system has two major components: the choroid plexus and the blood-brain barrier (BBB). The choroid plexus separates cerebrospinal fluid (CSF) from the bloodstream, and the BBB separates brain interstitial fluid (ISF) from blood.

The BBB has about 1000 times more surface area than the choroid plexus and is the primary obstacle to delivery of therapeutic compounds to the CNS. The BBB acts as a selective partition, regulating the exchange of substances between the CNS and the peripheral circulation. The primary structure of the BBB is the brain capillary endothelial wall. The tight junctions of brain capillary endothelial cells prevent circulating compounds from reaching the brain ISF by the paracellular route. Furthermore, recent work suggests the existence of a separate physiological barrier at the level of the basal lamina (Kroll et al. 1998). Other unique characteristics of the BBB include lack of intracellular fenestrations and pinocytic vesicles and a net negative charge on the luminal surface of the endothelium (Kroll et al. 1998).

The mechanisms by which substances traverse the BBB may generally be divided into active and passive transport mechanisms. Lipophilic molecules readily traverse the BBB by passive transport or diffusion through the endothelial plasma membranes, while hydrophilic molecules typically require an active transport system. Diffusion of many therapeutic compounds, across the BBB is also inhibited by size.

Many currently existing drug substances are unable to overcome these structural and metabolic barriers to enter the BBB in sufficient quantities to be efficacious. There is therefore a need for pharmaceutical compounds which can enable penetration of anti-cancer drugs through the BBB in sufficient amounts and at sufficient rates to be efficacious. Furthermore, many substances which, in theory, should be able to cross the BBB due to their lipophilicity, are not suitable for parenteral or oral delivery in the absence of potentially allergenic formulation ingredients. There is a need in the art for prodrugs which increase the solubility of drugs, preferably resulting in amphiphilic drugs which are orally available, soluble in the bloodstream, and which improve the ability of such drugs to enter the CNS. Conversely, there is a need in the art for prodrugs which increase the lipophilicity of hydrophilic drugs to produce amphiphilic prodrugs. Moreover, it is desirable that such amphiphilic prodrugs are hydrolyzed in vivo to release the active parent compound.

1.2.3 Strategies for Delivering Therapeutic Compounds to the CNS

Many attempts have been made in the art to deliver therapeutic compounds to the CNS with varying levels of success. Such attempts can generally be grouped into two categories: invasive and pharmacological.

Invasive delivery strategies include, for example, mechanical procedures, such as implantation of an intraventricular catheter, followed by pharmaceutical infusion into the ventricular compartment. Aside from general considerations relating to the invasiveness of mechanical procedures, a major difficulty with mechanical approaches is the lack of drug distribution. For example, injection of drugs into the CSF compartment commonly results in very little distribution beyond the surface of the brain. This lack of distribution is due in part to rapid exportation of drugs to the peripheral circulation.

Another invasive strategy for delivering therapeutic compounds to the CNS is by intracartoid infusion of highly concentrated osmotically active substances, such as mannitol or arabinose. Their high local concentration causes shrinkages of the brain capillary endothelial cells, resulting in a transient opening of the tight junctions which enable molecules to traverse the BBB. Such procedures have considerable toxic effects, including inflammation, encephalitis, etc. Furthermore, such procedures are not selective: the opening of the tight junctions of the BBB permits many undesirable substances to cross the BBB along with the therapeutically beneficial molecule. For a recent review of osmotic opening and other invasive means for traversing the BBB, see Kroll, Neurosurgery, Vol. 42, No. 5, May 1998.

There is therefore a need in the art for means for selectively enabling therapeutic agents, such as peptides, to cross the BBB in a controlled manner which permits accumulation of sufficient quantities of the therapeutic in the brain to induce the desired therapeutic effect.

The present inventors have surprisingly discovered that conjugation of small amphiphilic polymers to drugs, such as etoposide, solves many of the aforementioned difficulties. This approach relies on rational oligomer design using a hydrophobic component plus a hydrophilic component to balance the physiochemical properties of the parent molecule. By varying the molecular weight of the hydrophobic and hydrophilic components of the oligomer and/or the molecular weight of the amphiphilic portion of the oligomer, the overall physiochemical profile of the conjugated molecule can be systematically adjusted to produce the desired degree of amphiphilicity with concomitant alterations in solubility and pharmacokinetics.

The etoposide prodrugs of the present invention can effectively cross the blood-brain barrier. Based on the empirical data presented herein and on the results of our prior research described in U.S. patent application Ser. No. 09/134,803, entitled "Blood-Brain Barrier Therapeutics," the etoposide prodrugs are predicted to have improved oral bioavailability as well. These two elements, coupled with the ability to control the rate of hydrolysis of the prodrug from the drug compound, facilitate the use of chronic dosing regimens for the treatment of cancer of the CNS and other malignancies.

1.2.4 Treatment for CNS Tumors

The present inventors have surprisingly discovered that covalent modification of a hydrophobic drug with the oligomers of the present invention counteracts the hydrophobic nature of the parent compound and vastly improves its ability to penetrate the blood-brain barrier. Furthermore, the inventors have discovered that conjugation of a lipophilic parent drug, e.g., etoposide, with the oligomers of the present invention using a labile chemical bond that hydrolyzes in vivo, freeing the fully bioactive parent drug, improves solubility of the drug in the bloodstream and permits delivery of the drug to the CNS.

The prodrugs of the present invention exhibit the following useful properties:

The inactive prodrug form helps to mitigate administration-related toxicity;
A therapeutically significant amount of free drug reaches the CNS;
It is expected that the prodrug can be delivered to the CNS via the oral route;
The prodrug is more readily formulated in hydrophilic formulations;
The half-life of elimination of etoposide is extended; and
The conjugate has improved ability to pass from the intestine into the bloodstream.

1.2.5 Etoposide as a Treatment for CNS Tumors

Etoposide is a member of the epipodophyllotoxin class of compounds and is active against a broad spectrum of tumor types in vitro, including gliomas and astrocytomas (Giaccone, Gazdar et al. 1992; Kasahara, Fujiwara et al. 1992; Brown, McPherson et al. 1995; Chresta, Masters et al. 1996; Beauchesne, Bertand et al. 1998). Etoposide has a molecular weight of 589 daltons, is lipophilic and is nearly insoluble in water (Hande 1998). As a result, it is typically formulated in a mixture of benzyl alcohol, polysorbate 80/Tween 80, polyethylene glycol 300 and ethanol (VePesid®, Bristol Myers Squibb). For administration VePesid is diluted in physiologically compatible solutions to 0.2 mg(m to 0.4 mg/mL. Dose levels of 100 mg/m$^2$ to 600 mg/m$^2$ infused intravenously require volumes of 0.4 L to 5.1 L.

Although etoposide is hydrophobic, it does not readily penetrate the blood-brain barrier. As a result, concentrations of etoposide in brain parenchyma remain low after systemic administration (Hande, Wedlund et al. 1984; Donelli, Zucchetti et al. 1992; Kiya, Uozumi et al. 1992). Additionally, while etoposide can reach brain tumors, the concentration of etoposide in the tumor and surrounding tissue remain subtherapeutic (Donelli, Zucchetti et al. 1992). Due to the invasive nature of gliomas and astrocytomas and the difficulty of surgical resection, there is an urgent need for means for delivering drugs, such as etoposide, to areas of the brain that may harbor residual tumor cells.

One way to overcome the hydrophobicity of etoposide is to chemically modify the parent compound to increase its hydrophilicity. However, often such modifications destroy the desired biologic activity. Accordingly, there is a need in the art for amphiphilic etoposide prodrugs which increase penetration of the prodrug across the BBB and to thereby provide active etoposide to the CNS. Additionally, there is a need for a prodrug which facilitates delivery of etoposide into the CNS by other routes of administration, including oral administration. In rodent biodistribution studies, I.V. etoposide is found at significant concentrations in most non-CNS tissues, especially liver and kidney. However, its accumulation in the CNS is very low (Hande, Wedlund et al. 1984; Donelli, Zucchetti et al. 1992). The hydrophobicity of etoposide makes it a good substrate for the P-glycoprotein multidrug pump or related drug transporters found in the endothelium of CNS blood vessels (Schinkel, Smit et al. 1994; Schinkel, Wagenaar et al. 1996). Experimental evidence suggests that these drug transporters act as the element of the blood-brain barrier responsible for actively barring etoposide from the CNS (Abe, Hasegawa et al. 1994). These drug transporters appear also to be partly responsible for clearance of etoposide and other drugs from the blood via direct extrusion through the intestinal wall into the lumen (Leu and Huang 1995; Mayer, Wagenaar et al. 1997; Sparreboom, van Asperen et al. 1997). There is an urgent need in the art for etoposide prodrugs which have been modified to permit the delivery of therapeutic concentrations of etoposide to the CNS by disabling export of the prodrugs by the P-glycoprotein multidrug pump and related drug transporting of the CNS epithelium.

A considerable amount of effort has been devoted to developing extended dosing regimens for etoposide (Greco, Johnson et al. 1991; Hande 1998). These efforts were based on clinical studies demonstrating the superior response rates obtained with 3 to 5 day schedules of administration versus 1 day (Cavalli, Sonntag et al. 1978). Accordingly, there is a need in the art for prodrug versions of the etoposide which extend the metabolic half-life of etoposide.

Etoposide has been shown to be effective in vitro at concentrations as low as 0.1 g/mL (Kasahara, Fujiwara et al. 1992). However, removal of etoposide reverses its inhibition of topoisomerase II, allowing cells to recover (Joel 1996). In addition, etoposide's effect on topoisomerase II is toxic primarily in the G2 phase of the cell cycle. As a result, a relatively brief treatment with etoposide will kill cells in G2 but allow cells in other phases of the cell cycle to recover. Accordingly, there is a need in the art for etoposide prodrugs which permit chronic dosing, thereby extending treatment of a cycling cell population and leading to cell death of a much greater proportion of the population.

Due to the relatively brief half-life of etoposide, daily (or more often) I.V. infusions are needed to maintain plasma etoposide concentrations in the therapeutic range. Thus, there is a need for etoposide prodrugs which permit an oral dosing regimen with its convenience and lower cost. As noted above, studies with oral etoposide have determined that its bioavailability is erratic, leaving a physician with little assurance that the adequate dose had been delivered. Accordingly, a more consistently bioavailable etoposide prodrug is needed.

In summary, there is a need in the art for a means for permitting producing consistent bioavailability of drugs, such as etoposide, without the necessity of multiple, prolonged I.V. infusions. Furthermore, there is a need for prodrugs which provide anti-cancer agents, such as etoposide, with a sufficiently extended plasma half-life to maintain in vivo concentration in a therapeutic range. Finally, there is a need in the art for prodrugs which enable effective oral delivery of drugs, such as etoposide, and which enables such orally delivered prodrugs to cross the BBB to enter the CNS.

1.2.6 Toxicity and Formulation Problems Associated with Etoposide.

Researchers have modified the physiochemical and pharmacologic properties etoposide by covalently attaching chemical moieties. Etoposide phosphate (Etopophos®, Bristol Myers Squibb) contains a phosphate group at the 4'-position of etoposide, resulting in a prodrug with increased aqueous solubility. The phosphate group hydrolyzes rapidly in vivo, and the compound has the same pharmacologic profile as etoposide. The improved water solubility of this etoposide analog increases the convenience of intravenous infusion; however, the oral bioavailability is only slightly improved, and the variability in bioavailability is still high, presumably because etoposide phosphate is converted into etoposide rapidly in the gut.

Several researchers have pursued formulation of cytotoxic drugs such as paclitaxel, adriamycin and doxorubicin in liposomal or micellar form. One objective of these strategies has been to create "sustained release" etoposide, producing extended periods of plasma etoposide concentrations in the therapeutic range. A second objective has been to sequester drugs in these vehicles to restrict access to non-target tissues. However, due to the large size of these particles, it is unlikely that this approach will facilitate improved oral bioavailability or penetration of the BBB. Accordingly, a need remains for etoposide prodrugs which facilitate improved oral bioavailability as well as penetration of the BBB.

A third approach is to conjugate the drug molecule to hydrophilic polymers to improve its solubility. Both polyethylene glycol (PEG) and polyglutamate have been used as hydrophilic polymers in this strategy. It appears that both polymers will increase the solubility of etoposide and therefore improve its handling characteristics. However, the conjugated polymers have been relatively large, resulting in etoposide prodrugs with altered pharmacokinetics and low drug loading. There is therefore a need in the art for etoposide prodrugs with smaller polymers, which prodrugs have improved solubility characteristics as well as the other advantageous attributes described above.

2. SUMMARY OF THE INVENTION

The present invention generally provides amphiphilic prodrugs comprising a drug joined by hydrolyzable bond(s) to one or more straight or branched PEG-oligomer(s) having from 1 to 25 polyethylene glycol units. The PEG-oligomer preferably comprises a salt-forming moiety, which is preferably selected from the group consisting of ammonium and carboxylate. The PEG-oligomers are preferably joined to the therapeutic compound by a bond, such as ester or carbonate, which is hydrolyzable in vivo.

In another aspect of the present invention, the drug portion of the amphiphilic prodrug is etoposide or an etoposide analogue which retains some or all of the therapeutic activity of etoposide.

The amphiphilic prodrug of claim may be derivatized by as many PEG-oligomers as there are sites on the drug for attachment of such PEG-oligomers. Thus, for- example, etoposide has 3 sites and can therefore be derivatized by 1, 2 or 3 of the PEG-oligomers.

In another aspect, the amphiphilic prodrugs can be delivered via the oral route of administration to provide a therapeutically effective dose of the drug to the bloodstream. Furthermore, in another aspect, the orally delivered derivatives can provide a therapeutically effective dose of the therapeutic compound to the CNS.

The present invention also provides pharmaceutical compositions comprising the amphiphilic prodrugs of the invention in association with a pharmaceutically acceptable carrier. Such pharmaceutical compositions may be formulated so as to be suitable for oral administration, and may be in any of a wide variety of dosage forms known in the art, such as tablets, capsules, caplets, gelcaps, pills, liquid solutions, suspensions or elixirs, powders, lozenges, micronized particles and osmotic delivery systems.

In another aspect, the present invention provides a amphiphilic prodrug comprising a drug joined by hydrolyzable bond(s) to one or more PEG-oligomer(s) selected from the group consisting of any of the oligomers of Formulae 1–11.

Any of the foregoing oligomers of Formulae 1–11 may also suitably comprise a salt-forming moiety. Preferred salt-forming moieties are ammonium and carboxylate. The preferred drugs are etoposide and etoposide analogues which retain some or all of the therapeutic activity of etoposide, or which exhibit improved activity as compared to etoposide. The drug is derivatized by the number of PEG-oligomers which does not exceed the number of sites of attachment for such PEG-oligomers. Thus where the amphiphilic prodrug is etoposide, it can be derivatized by 1, 2 or 3 of the PEG-oligomers of Formulae 1–11.

The present invention also provides pharmaceutical compositions comprising a amphiphilic prodrug of Formulae 1–11 and a pharmaceutically acceptable carrier. The pharmaceutical composition can be formulated to be suitable for oral administration, and can be in any of a variety of pharmaceutical dosage forms, such as tablets, capsules, caplets, gelcaps, pills, liquid solutions, suspensions or elixirs, powders, lozenges, micronized particles and osmotic delivery systems.

The present invention also provides a method for treating a mammalian subject having a etoposide-responsive disease condition comprising administering to the patient therapeutically effective amount of a amphiphilic prodrug comprising at least one therapeutic compound; and one or more PEG polymers and/or oligomers, each joined to the therapeutic compound by a hydrolyzable bond, said PEG polymers and/or oligomers each comprising one or more straight or branched PEG segments consisting of 2 to 25 polyethylene glycol units. The oligomers optionally comprise a salt-forming moiety.

The present invention also provides a method for treating a mammalian subject having a etoposide-responsive disease condition comprising administering to the patient of therapeutically effective amount of a drug derivativized by any of the Formulae 1–11.

In one aspect of the methods of treatment, the amphiphilic prodrug is delivered via an oral route of administration to provide a therapeutically effective dose of the drug to the bloodstream. In another aspect, the amphiphilic prodrug is delivered via a parenteral route of administration and provides a therapeutically effective dose of the drug to the brain. In yet another aspect, the amphiphilic prodrug is delivered via an oral route of administration and provides a therapeutically effective dose of the drug to the brain. Furthermore, the amphiphilic prodrug may be administered in association with a pharmaceutically acceptable carrier.

In a further aspect, diseases treated according to the therapeutic methods of the invention include cancers, tumors and malignancies, such as acute myelocytic leukemia, bladder carcinoma, breast cancer, cancers of the gastrointestinal tract, Ewing's sarcoma, Hodgkin's lymphomas, Kaposi's sarcoma, leukemias, lung carcinoma, lymphomas, non-Hodgkin's lymphomas, ovarian cancer, small cell lung cancers and testicular carcinoma.

2.1 Definitions

As used herein the terms "PEG" refers to straight or branched polyethylene glycol polymers and monomers. The term "PEG-oligomer" refers to oligomers comprising PEG polymers which have been modified to include groups which do not eliminate the amphiphilic properties of such polymers, e.g., without limitation, alkyl, aryl, amino-alkyl and amino-aryl; see also Formulae 2–11 set forth in Section 4, "Detailed Description of the Invention." The term "PEG subunit" or "PEG unit" refers to a single polyethylene glycol unit, i.e.: —($CH_2CH_2O$)—. The term "PEG oligomer/polymer" as used herein refers to PEG oligomers and/or PEG polymers.

As used herein terms such as "non-hydrolyzable" and phrases such as "not hydrolyzable" are used to refer to bonds which cannot be hydrolyzed under normal physiological conditions, as well as bonds which are not quickly hydrolyzed under normal physiological conditions, such as carbamate and amide bonds. The term "hydrolyzable" refers to bonds which are hydrolyzed under normal physiological conditions, such as ester and carbonate bonds.

A "therapeutically effective" amount or dose is an amount or dose which prevents, delays or reduces the severity of the onset of disease or other adverse medical condition, or an amount necessary to arrest or reduce the severity of an ongoing disease or other adverse medical condition, and also includes an amount necessary to enhance normal physiological functioning.

As used herein, "pharmaceutically acceptable" component (such as a salt, carrier, excipient or diluent) of a formulation according to the present invention is a component which (1) is compatible with the other ingredients of the formulation in that it can be combined with the prodrugs of the present invention without eliminating the biological activity of the prodrugs; and (2) is suitable for use in animals (including humans) without undue adverse side effects (such as toxicity; irritation, and allergic response). Side effects are "undue" when their risk outweighs the benefit provided by the pharmaceutical composition. Examples of pharmaceutically acceptable components include, without limitation, any of the standard pharmaceutical carriers such as phosphate buffered saline solutions, water, emulsions such as oil/water emulsion, microemulsions and various types of wetting agents.

3. BRIEF DESCRIPTION OF THE DRAWINGS

FIG. 1. Structure of etoposide showing reactive hydroxyl groups that can be used as sites of attachment for the oligomers of the present invention.

Figure 2:
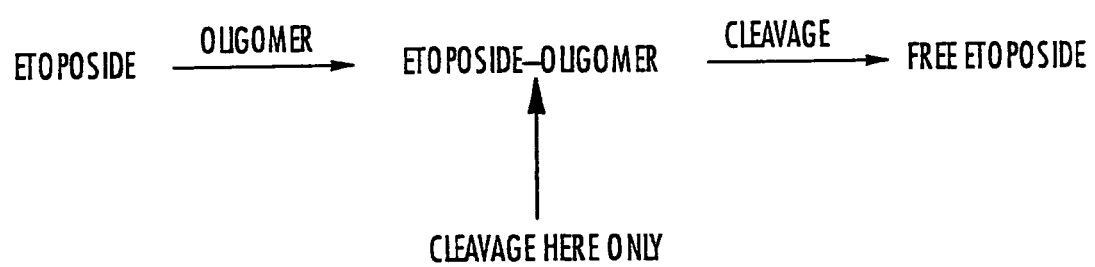

FIG. 2. General scheme of the operation of the present invention. The PEG-oligomer/polymer is attached to the hydroxyl groups on etoposide via a labile ester bond. In the bloodstream, the hydrolyzable bond is cleaved, thereby freeing the active parent compound.

Figure 3:
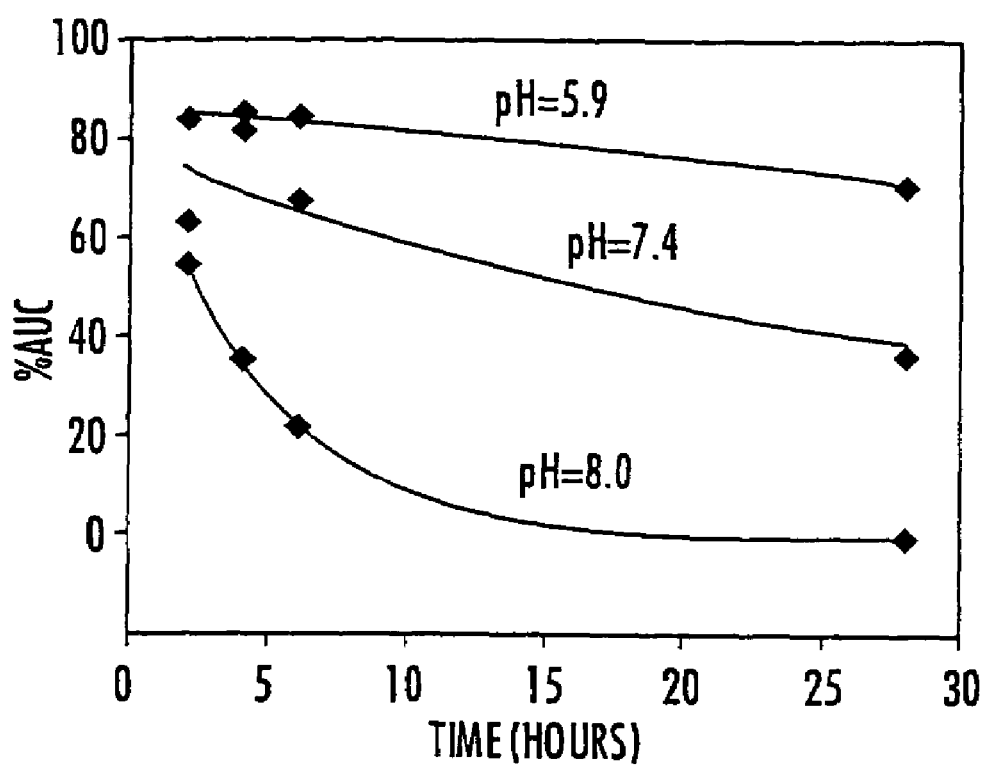

FIG. 3. Cleavage of conjugates in an aqueous environment. Samples of purified etoposide conjugate in phosphate buffers show increasing rate of hydrolysis as the pH increases. At pH 5.9 approximately 10% of the conjugate is hydrolyzed in 28 hours, while at pH 7.4 approximately 40% is hydrolyzed in the same time period. At pH 8.0 hydrolysis is essentially complete after 20 hours. No significant side products were observed during this conversion.

Figure 4:
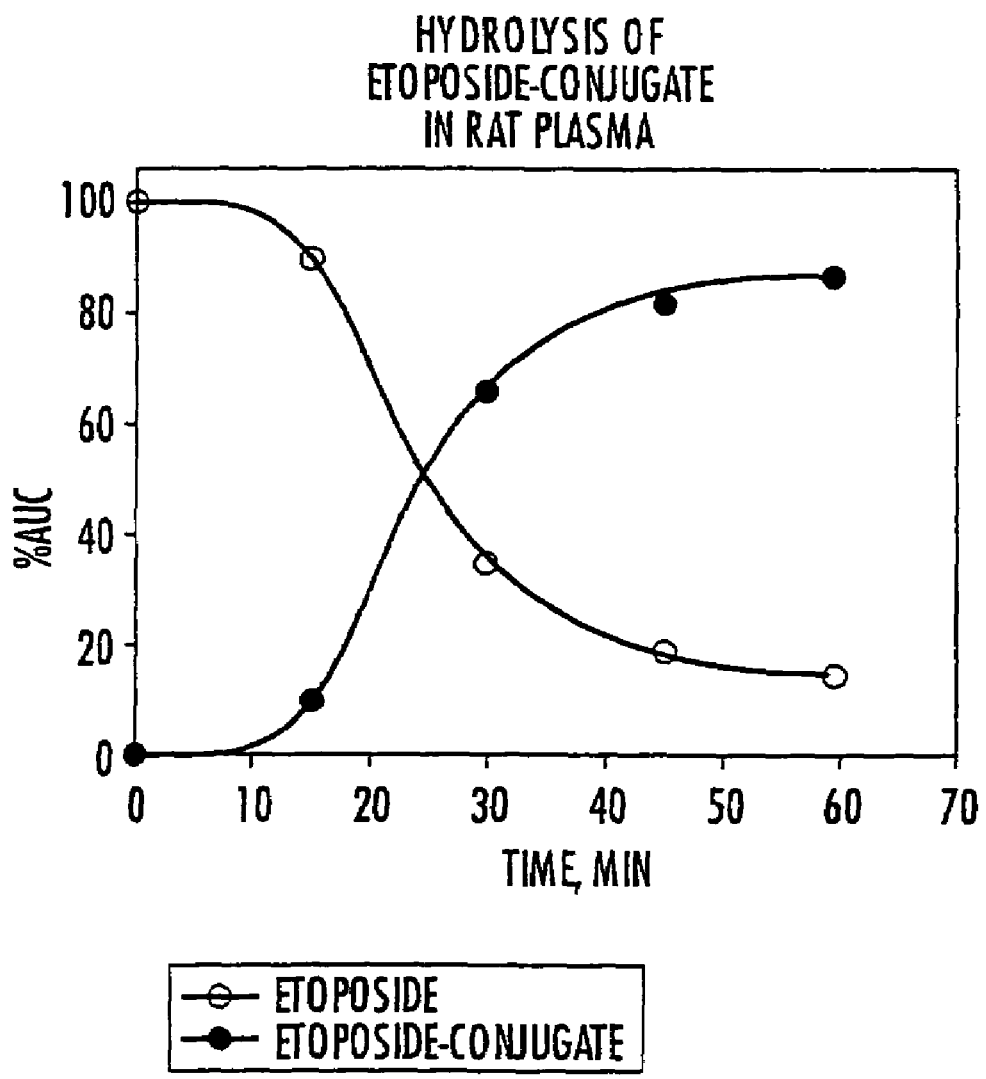

FIG. 4. Graph showing that when the etoposide conjugate was incubated in fresh rat plasma at 37° C. hydrolysis of the conjugated etoposide and appearance of free etoposide showed reciprocal behavior, indicating that hydrolysis of the PEG-oligomer/polymer etoposide conjugate is complete and releases free, active etoposide.

Figure 5:
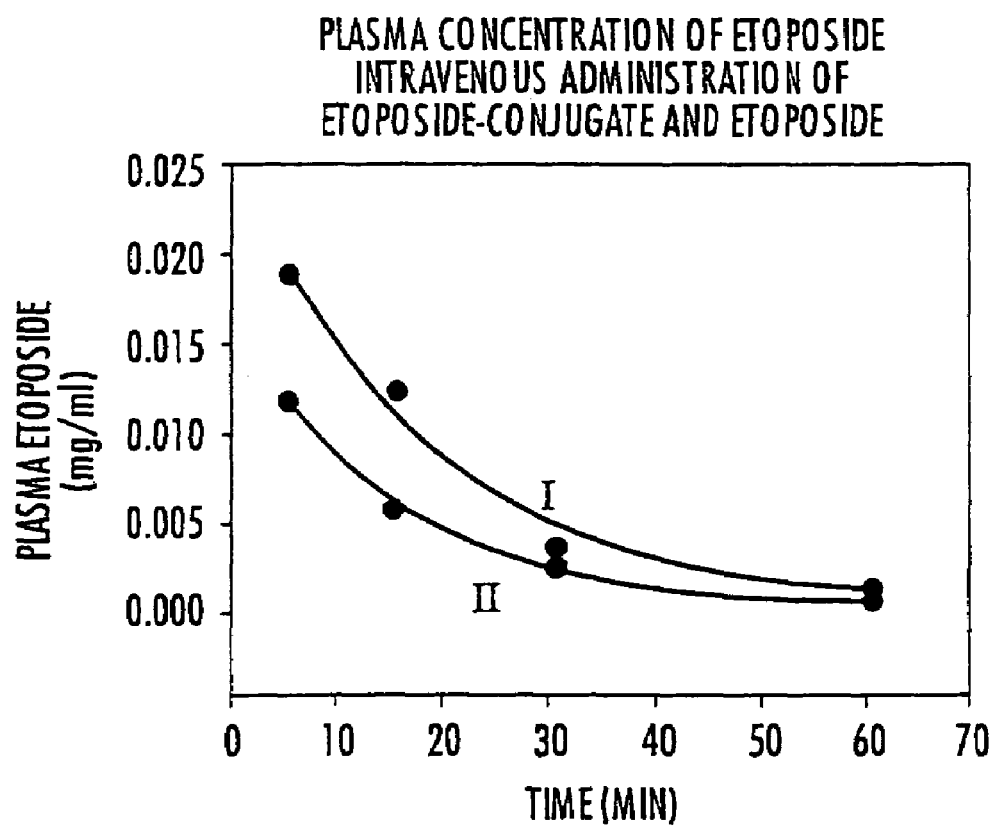

FIG. 5. Graph showing in vivo profile of rats given etoposide conjugate versus rats given etoposide. Conjugates of etoposide were administered I.V. to Sprague Dawley rats at 9 µmol/kg. Measurement of free etoposide in plasma at various time points demonstrated that peak plasma etoposide concentration was increased by 60% and the half-life was extended by approximately 50% in rats given the etoposide conjugate (curve I) versus rats given etoposide (curve II).

Figure 6:
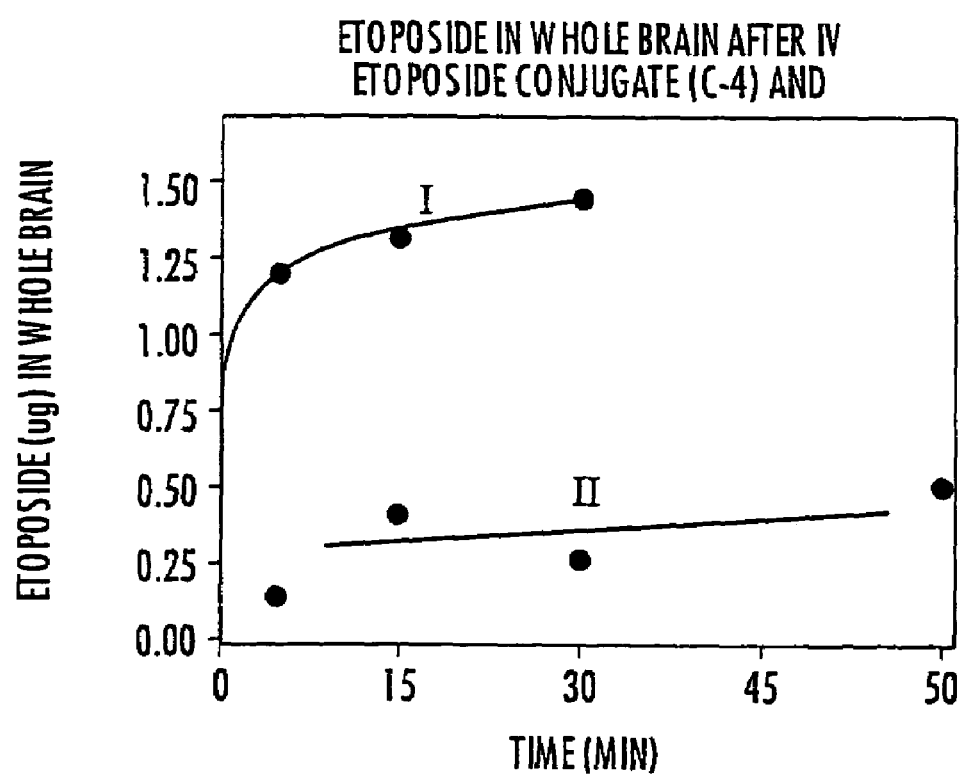

FIG. 6. When the etoposide concentration in brain tissue was measured in these rats the data revealed that injection with the etoposide conjugate led to a 3-fold increase in accumulation of free etoposide in the brain parenchyma, demonstrating an increased penetration of the blood-brain barrier by conjugated peptide hormones.

4. DETAILED DESCRIPTION OF THE INVENTION

The ensuing detailed description is divided into sections for ease of reference only. Subject headings are not intended to limit the scope of the invention.

4.1 Prodrugs of the Invention

The present invention provides drug-PEG oligomer/polymer prodrugs. The prodrugs of the present invention generally comprise a drug component and a PEG-oligomer/polymer component. The prodrugs are useful in facilitating the formulation of drugs, the oral delivery of drugs, and the delivery of drugs across the BBB. These advantages are facilitated by increasing the amphiphilicity of the molecule.

Thus, if the drug molecule is hydrophylic, the PEG-oligomer/polymer increases lipophilicity and thereby improves the amphiphilicity of the prodrug. Conversely, where the drug is lipophilic, the PEG-oligomer/polymer increases the hydrophilicity of the drug and thereby provides a more amphiphilic prodrug. The PEG-oligomer/polymer is attached to the drug by a bond that hydrolyzes under normal physiological conditions to release the active parent compound.

4.1.1 Drug Component of the Prodrugs

The prodrugs of the present invention comprise a drug component. Suitable drug components are therapeutic compounds with free hydroxy, thio, phosphate or amino groups, which serve as sites of attachment for the oligomers. Preferred drug components are epipodophyllotoxins, and analogues thereof, such as etoposide, teniposide and etoposdide phosphate. The structural formula of etoposide is set forth in FIG. 1.

In one aspect of the present invention, the drug component is an etoposide analogue. Many analogues of etoposide are known in the art, which are more or less effective than etoposide itself. The present invention contemplates the use of any etoposide analogue which does not have completely diminished activity.

Other drugs suitable for use in the prodrugs include paclitaxel and docetaxel. Still others are listed in U.S. Pat. No. 5,795,909, which is incorporated herein by reference.

4.1.2 PEG-Oligomers/Polymers

The amphiphilic PEG-oligomers/polymers of the prodrugs of the present invention may be straight or branched. Preferred oligomers/polymers comprise PEG polymers having from 2 to 25 PEG units, more preferably from 2 to 20 PEG units, still more preferably from 2 to 15 PEG units. Ideally, the PEG polymer has from 2 to 10 PEG units. In another aspect, the PEG polymer has a molecular weight which is not greater than 1000.

In a preferred mode, the PEG polymers have the formula:

$$—(CH_2CH_2O)_X—CH_3 \qquad \text{(Formula 1)};$$

wherein X=2–25.

In a more preferred mode, X in Formula 1 is from 2 to 25, and in a still more preferred mode, from 2–20, still more preferably from 2–15, most preferably from 2–10. Ideally, X is 2, 3, 4, 5, 6, 7, 8, 9 or 10.

Preferred PEG oligomers are selected from the group consisting of:

(Formula 2)

wherein n is from 1 to 7, m is from 2 to 25, and R is a lower alkyl preferably selected from the group consisting of hydrogen, methyl, ethyl, propyl, isopropyl and t-butyl;

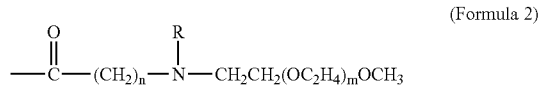
(Formula 3)

wherein n is from 1 to 6, p is from 2 to 8, m is from 2 to 25, and R is a lower alkyl, preferably selected from the group consisting of hydrogen, methyl, ethyl, propyl, isopropyl and t-butyl;

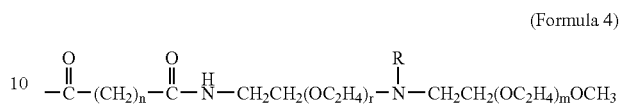
(Formula 4)

wherein n is from 1 to 6, m and r are each independently from 2 to 25, and R is a lower alkyl, preferably selected from the group consisting of hydrogen, methyl, ethyl, propyl, isopropyl and t-butyl;

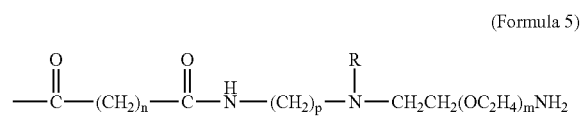
(Formula 5)

wherein n is from 1 to 6, p is from 2 to 8 and m is from 2 to 25 and R is a lower alkyl, preferably selected from the group consisting of hydrogen, methyl, ethyl, propyl, isopropyl and t-butyl;

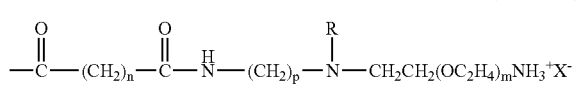
(Formula 6)

wherein n is from 1 to 6, p is from 2 to 8, m is from 2 to 25, $X^-$ is a negative ion, preferably selected from the group consisting of chloro, bromo, iodo, phosphate, acetate, carbonate, sulfate, tosylate and mesylate, and R is a lower alkyl, preferably selected from the group consisting of hydrogen, methyl, ethyl, propyl, isopropyl and t-butyl,

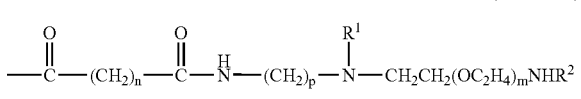
(Formula 7)

wherein n is from 1 to 6, p is from 2 to 8, m is from 2 to 25, and $R^1$ and $R^2$ are each independently a lower alkyl, preferably selected from the group consisting of methyl, ethyl, propyl, isopropyl, and t-butyl;

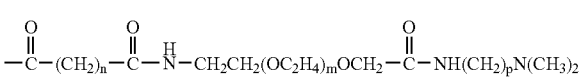
(Formula 8)

wherein n is from 1 to 6, p is from 2 to 8 and m is from 2 to 25;

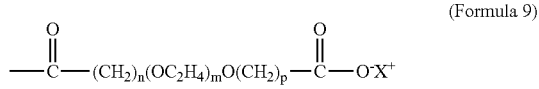
(Formula 9)

wherein n and p are each independently from 1 to 6, m is from 2 to 25 and X⁺ is a positive ion, preferably selected from the group consisting of hydrogen, sodium, potassium, calcium, lithium and ammonium salts;

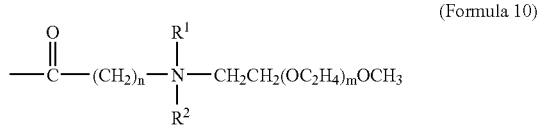
(Formula 10)

wherein n is from 1 to 5, m is from 2 to 25, and wherein $R^1$ and $R^2$ are each independently lower alkyl and are preferably independently selected from the group consisting of hydrogen, methyl, ethyl propyl, isopropyl and t-butyl; and

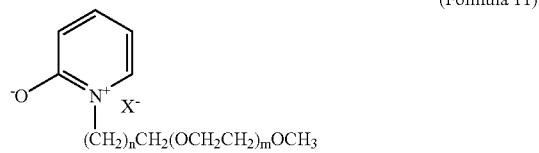
(Formula 11)

wherein n is from 1 to 6, m is from 2 to 25 and X⁻ is a negative ion, preferably selected from the group consisting of chloro, bromo, iodo, phosphate, acetate, carbonate, sulfate, tosylate and mesylate.

In any of the foregoing Formulae 1–11, the total number of PEG units is preferably from 2 to 25, more preferably from 2–20, still more preferably from 2–15, most preferably from 2–10. Ideally, the total number of PEG units is 2, 3, 4, 5, 6, 7, 8, 9 or 10. In formulae, such as Formula 4, which contain two PEG polymer segments, the preferred number of PEG units set forth in this paragraph may be contained completely in either of the two PEG polymer segments or may be distributed between the two PEG polymer segments.

The PEG-oligomer/polymer may also comprise one or more salt forming moieties. Preferred salt forming moieties are ammonium and carboxylate. Suitable salts also include any pharmaceutically acceptable acid-addition salts for PEG-oligomers/polymers having a basic amino group and pharmaceutically acceptable salts derived from pharmaceutically acceptable bases for PEG-oligomers/polymers having, e.g., a free carboxy group. Pharmaceutically acceptable salts of the acid may be prepared by treating the free acid with an appropriate base. Pharmaceutically acceptable base salts include, for example, alkali metal salts such as sodium or potassium, alkaline earth metal salts such as sodium or potassium, alkaline earth metal salts such as calcium or magnesium, and ammonium or alkyl ammonium salts.

4.1.3 Attachment of Lipophilic Drug to PEG-Oligomers/Polymers

A key feature of the approach of the present invention is the nature of the chemical bond that joins the PEG-oligomer/polymer to etoposide. First, the parent drug must be protected and delivered by the oligomer, then hydrolysis of the joining bond must free the active parent drug. Second, the type of chemical bond used to join the two moieties should be chosen to enable in vivo hydrolysis, resulting in the release of a therapeutically effective amount of the active parent drug. Preferred hydrolyzable bonds include ester and carbonate.

The PEG-oligomers/polymers are suitably attached to the parent drug at any of the free hydroxy, thio, phosphate or amino groups of the parent drug compound. FIG. 1 shows appropriate points of attachment for the oligomers to the etoposide molecule. It will be appreciated by those of skill in the art that a solution of prodrugs according to the present invention where the drug is etoposide or the like may comprise a mixture of 1-, 2-, and/or 3-substituded prodrugs.

4.2 Methods for Producing the Etoposide-PEG Conjugates

Etoposide is commercially available and can be prepared by known synthetic methods. In the ensuing examples, the n, m, p and R symbols and the like are as described in general Formulae 1–11.

4.2.1 Formula 1

The polymers of Formula 1 are commercially available and/or are readily synthesized by one of skill in the art without undue experimentation.

4.2.2 Formula 2

In the synthesis of the oligomers of Formula 2:

(Formula 2)

wherein n is from 1 to 7, m is from 2 to 25, and R is a lower alkyl, it is desirable to start with an ester of a fatty acid having a terminal carbon which bears a primary amino moiety. Such compounds are commercially available. The amino ester in an inert solvent is treated with a solution of monomethoxy polyethylene glycol of appropriate molecular weight bearing an aldehyde terminal carbon, followed by the addition of a solution of sodium borohydride. The product is purified after solvent extraction by column chromatography.

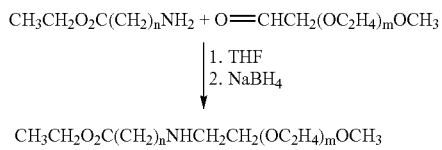

where n and m are as previously defined.

Sometimes it is desirable to alkylate the secondary amine moiety to form a desired oligomer bearing a tertiary amine. A solution of the oligomer in an inert solvent is treated with one equivalent of alkyl halide. The product is purified after solvent extraction by column chromatography.

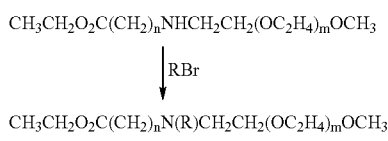

The ester is converted to an acid by treating it in an inert solvent with a dilute solution of sodium hydroxide at room temperature. The free acid is purified after solvent extraction by column chromatography. The acid is coupled to the drug after in situ activation.

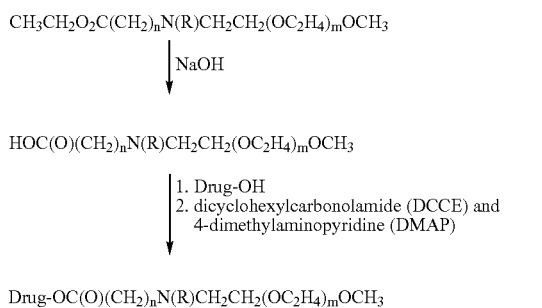

The drug in these examples can be, for example, etoposide.

It is sometimes desirable to synthesize the drug-oligomer by starting with the therapeutic compound derivatized as an ester of fatty acid having a terminal carbon which bears a halide and an appropriate monomethoxy-polyethylene glycol with a terminal carbon bearing a primary amino moiety. The polyethylene glycol reagent is dissolved in an inert solvent at room temperature. An equivalent amount of the drug-halide is dissolved in an inert solvent and added slowly to the solution of polyethylene glycol. The product is purified after solvent extraction using column chromatography.

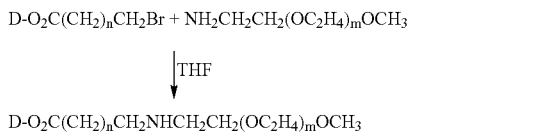

The ester is hydrolyzed with a dilute solution of sodium hydroxide as in the previous procedure and coupled to the drug (e.g., etoposide) after in situ activation as in the previous example.

4.2.3 Formula 3

In the synthesis of the oligomer of Formula 3:

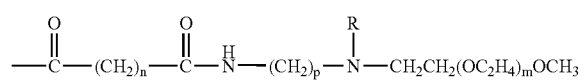

(Formula 3)

wherein n is from 1 to 6, p is from 2 to 8, m is from 2 to 25, and R is a lower alkyl, it is desirable to start with a half-ester of a dicarboxylic acid of an aliphatic compound and an amino-containing polyethylene. In the synthesis of the amino-containing polyethylene, an appropriate molecular weight monomethyl polyethylene glycol having an aldehyde moiety at the terminal end is treated in an inert solvent with an aliphatic compound bearing amino moieties at the two terminal carbons. One amino moiety is protected with tert-butoxycarbonyl while the free amine reacts with the aldehyde moiety. The product is purified after solvent extraction column chromatography. The product is deprotected by treating in an inert solvent with trifluoroacetic acid, neutralizing the acid and purifying after solvent extraction using column chromatography.

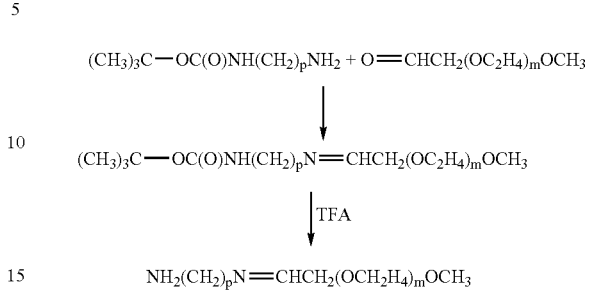

The half ester in an inert solvent is treated with a solution of the amino-derivatized polyethylene glycol at room temperature after an in situ activation of the acid. The product is purified by column chromatography after solvent extraction. The imino moiety is reduced by treating with a solution of sodium borohydride and purified as in the previous procedure.

It is sometimes desirable to alkylate the secondary amine. To achieve this end, the oligomer is dissolved in an inert solvent and treated with a solution of an alkyl halide in an inert solvent.

The ester is hydrolyzed, activated in situ, and coupled to the therapeutic compound (e.g., etoposide).

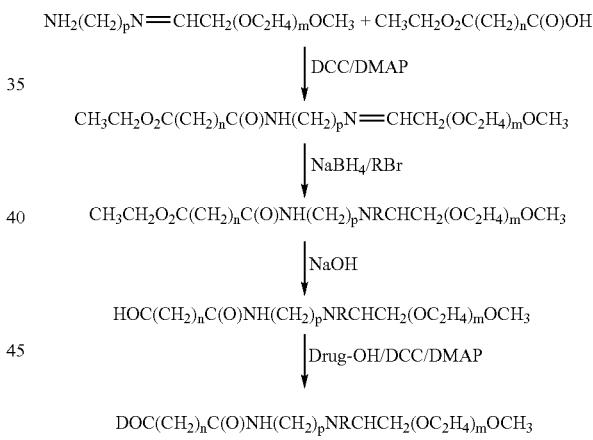

where D indicates the drug component of the drug-amphiphilic conjugate. The amphiphilic drug conjugate is converted to a salt form to improve aqueous solubility as necessary using a pharmaceutically acceptable acid.

4.2.4 Formula 4

The procedure for the synthesis of the oligomer of Formula 4:

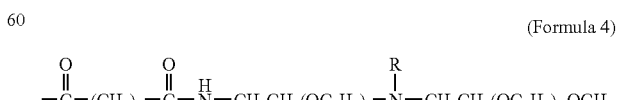

(Formula 4)

wherein n is from 1 to 6, m and r are each independently from 2 to 25, and R is a lower alkyl, is the same as for the oligomer of Formula 3 with the exception that the aliphatic diamino moieties are replaced with polyethylene glycol diamine.

4.2.5 Formula 5

In the synthesis of a prodrug comprising the oligomer of Formula 5:

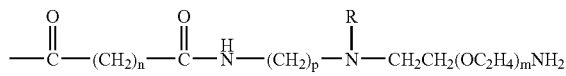

(Formula 5)

wherein n is from 1 to 6, p is from 2 to 8 and m is from 2 to 25 and R is a lower alkyl, the drug bearing a hydroxyl moiety is treated in an inert solvent with an aliphatic acid anhydride to form a half ester. The half-ester is dissolved in an inert solvent, activated and treated with one equivalent of a polyethylene glycol of appropriate molecular weight, in which the terminal hydroxyl moieties are replaced with amino moieties.

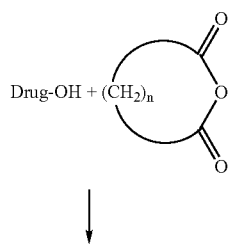

$Drug-OH + (CH_2)_n$

↓

$Drug-OC(O)(CH_2)_nC(O)OH$ 1. 1,1′-carbonyldiimidizole (CDI)
2. $NH_2(CH_2)_pNRCH_2CH_2(OC_2H_4)_mNHC(O)OC(CH_3)_3$
3. TFA/Basic Column

↓

$Drug-OC(O)(CH_2)_nC(O)NH_2CH_2CH_2(OC_2H_4)_mNH_2$ where all substituent groups (e.g., n, m and p) are as previously defined.

4.2.6 Formula 6

The oligomer of Formula 6:

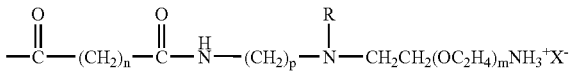

(Formula 6)

wherein n is from 1 to 6, p is from 2 to 8, m is from 2 to 25, $X^-$ is a negative ion, is prepared by treating the compound represented by Formula 5 with a pharmaceutically acceptable acid to obtain the appropriate salt. The salt increases the water-solubility of the amphiphilic drug conjugate.

4.2.7 Formula 7

The synthesis of the oligomer of Formula 7:

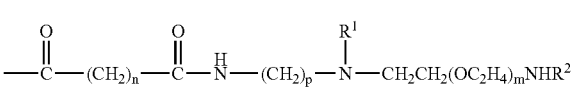

(Formula 7)

wherein n is from 1 to 6, p is from 2 to 8, m is from 2 to 25, and $R^1$ and $R^2$ are each independently a lower alkyl, is analogous to the synthesis of the oligomer of Formula 5, with the exception that the end-terminal amino moiety is alkylated with the halide of a short chain alkyl group such as methyl, ethyl, propyl, isopropyl or t-butyl before reacting to the half-ester of the drug.

$(CH_3)COC(O)NH_2(CH_2)_pBr + NH_2CH_2CH_2(OC_2H_4)_mNH_2$

↓

$(CH_3)_3COC(O)NH_2(CH_2)_pNHCH_2CH_2(OC_2H_4)_mNH_2$

1. RBr
2. TFA
3. Basic Column
4. $D-O_2C(CH_2)_nCO_2H/DCC$ $D-OC(O)(CH_2)_nC(O)NH(CH_2)_pNRCH_2CH_2(OC_2H_4)_mNHR$ where n, m and R are as previously defined.

4.2.8 Formula 8

In the synthesis of the oligomer of Formula 8:

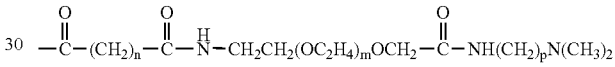

(Formula 8)

wherein n is from 1 to 6, p is from 2 to 8 and m is from 2 to 25, the half-ester of the aliphatic dicarboxylic acid is treated in an inert solvent with polyethylene glycol that has already been derivatized with amino moieties, after in situ activation.

$CH_3CH_2OC(O)(CH_2)_nC(O)OH$
+
$NH_2CH_2CH_2(OCH_2CH_2)_mOCH_2C(O)NH(CH_2)_pN(CH_3)_2$

1. DCC;
2. NaOH $HOC(O)(CH_2)_nC(O)NHCH_2CH_2(OCH_2CH_2)_mOCH_2C(O)NH(CH_2)_pN(CH_3)_2$

The amino-derivatized polyethylene glycol is prepared from an N-protected polyethylene glycol amino acid.

$tert-BOCNHCH_2CH_2(OCH_2CH_2)_mOCH_2C(O)-OH + NH_2(CH_2)_pN(CH_3)_2$

↓ DCC/DMAP $tert-BOCNHCH_2CH_2(OCH_2CH_2)_mOCH_2C(O)-NH(CH_2)_pN(CH_3)_2$

↓ TFA/Basic Column $NH_2CH_2CH_2(OCH_2CH_2)_mOCH_2C(O)-NH(CH_2)_pN(CH_3)_2$

The primary amino moiety is deprotected with trifluoroacetic acid and basified before treating with the half-ester;

4.2.9 Formula 9

In the synthesis of the oligomer of Formula 9:

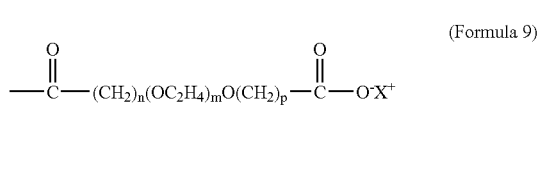
(Formula 9)

wherein n and p are each independently from 1 to 6, m is from 2 to 25 and $X^+$ is a positive ion, the starting acid is commercially available. It is sometimes desirable to prepare the diacid. To achieve this end, the appropriate modified polyethylene glycol oligomer is treated in an inert solvent with sodium hydride and an ester of a fatty acid bearing a halide moiety at the terminal carbon. The carboxylic acid diester is hydrolyzed in a dilute solution of sodium hydroxide and coupled to the drug moiety after in situ activation. The desired product is separated and purified by column chromatography.

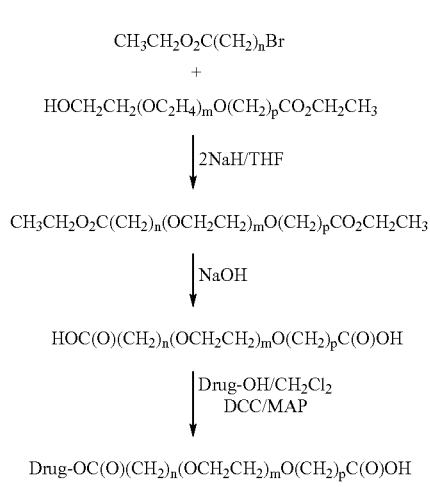

where n, m and p are as previously defined.

4.2.10 Formula 10

The synthesis of the oligomer of Formula 10:

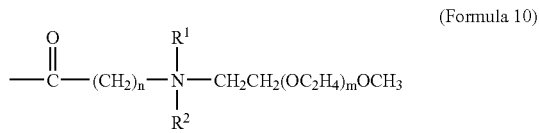
(Formula 10)

wherein n is from 1 to 5, m is from 2 to 25, and wherein $R^1$ and $R^2$ are each independently lower alkyl, is analogous to the synthesis of the oligomer of Formula 2, with the exception that the amino moiety is quaternized with short-chain aliphatic moieties. It is noted that the methoxy moiety can include other short chain (1 to 6 carbons) aliphatic moieties.

4.2.11 Formula 11

In the synthesis of the oligomers of Formula 11:

(Formula 11)

wherein n is from 1 to 6, m is from 2 to 25 and $X^-$ is a negative ion, a 2-fluoro- or 4-fluoro-pyridine is treated in an inert solvent with a monomethoxypolyethylene glycol having a terminal carbon bearing a halide, tosylate or mesylate ion. This pyridinium derivative is precipitated and triturated with an appropriate solvent and dried. The salt in an inert solvent is treated with drug, such as etoposide, in the presence of a quaternary-salt compound forming base, to yield a polyethylene glycol pyridinium derivative.

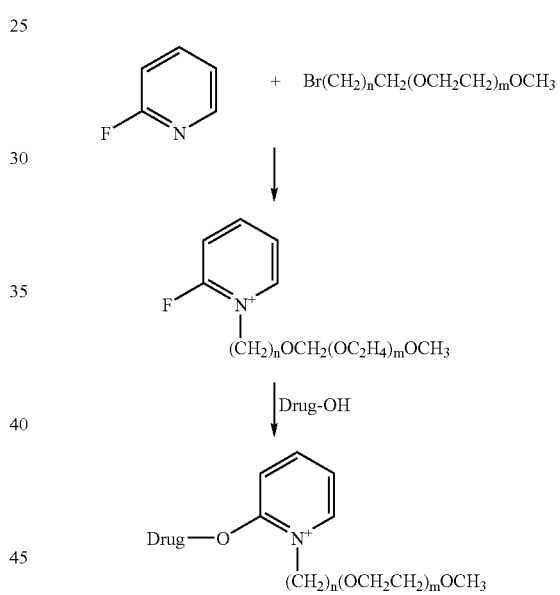

4.2.12 Attachment of PEG Polymers/Oligomers to the Therapeutic Compound

The following procedure is illustratively given using etoposide as an example; however, the procedure will be understood by those of skill in the art to have applicability to other therapeutic compounds as well. The PEG-oligomers/polymers of the present invention can be attached to etoposide according to the following general synthetic procedure. Etoposide is dissolved in a substantially dry organic solvent, e.g., chloroform. Pyridine or another quaternary-compound forming agent is added to the foregoing mixture. Activated PEG-oligomer/polymer is added dropwise and the mixture is stirred for 3–5 hours. Then reaction mixture is washed with 1% $H_2SO_4$ and deionized water, dried over $MgSO_4$ and concentrated. The residue is chromatographed on silica gel column, using-for example, chloroform-methanol (90%-10%) as developing agent. The fractions containing the desired prodrugs are collected, concentrated, and dried. Product is characterized by TLC, HPLC, NMR, and/or MS.

4.3 Pharmaceutical Compositions and Methods of Use

The pharmaceutical compositions containing the novel prodrugs as active ingredients may be any pharmaceutically acceptable dosage forms known in the art which do not completely diminish the activity of the prodrugs. Examples include oral, injectable or I.V. dosage forms. Each dosage form comprises an effective amount of a prodrug and pharmaceutically inert ingredients, e.g., conventional excipients, vehicles, fillers, binders, disintegrants, solvents, solubilizing agents, sweeteners, coloring agents and any other inactive ingredients which are regularly included in pharmaceutical dosage forms. Suitable oral dosage forms include tablets, capsules, caplets, gelcaps, pills, liquid solutions, suspensions or elixirs, powders, lozenges, micronized particles and osmotic delivery systems. Suitable injectable and IV dosage forms include isotonic saline solutions or dextrose solutions containing suitable buffers and preservatives. Many such dosage forms and vehicles, and listings of inactive ingredients therefor, are well-known in the art and are set forth in standard texts such as *The Pharmaceutical Codex: Principles and Practice of Pharmaceutics*, $12^{th}$ edition (1994).

The present invention also comprehends a method of treating a mammalian subject having a tumor, cancer, or other disease condition responsive to the specific therapeutic compound (e.g., an anti-cancer drug such as etoposide). The method comprises administering to said subject a pharmaceutical composition containing a pharmaceutically effective amount of the drug-oligomer prodrug according to the present invention. Diseases/conditions which may be treated by the invention include, without limitation, cancers, tumors and malignancies. Diseases/conditions which may be treated by the invention also include, without limitation, small cell lung cancer, non-small cell lung cancer, testicular cancer, lymphoma, leukemia, ovarian cancer (specifically including relapsed or platinum refractory ovarian cancer), and gastric cancer.

The prodrugs of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the prodrugs of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral administration is generally preferred for administration to a human. In some cases, a relatively lower dose is sufficient and, in some cases, a relatively higher dose or increased number of doses may be necessary. Topical application similarly may be once or more than once per day depending upon the usual medical considerations. Advantageously, prodrugs of the present invention may be administered in a single daily dose, or the total daily dosage may be administered in divided doses of two, three or four times daily.

In the methods of the present invention, the prodrugs can form the active ingredient and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the drug-oligomer prodrug, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The prodrugs of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The prodrugs of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Prodrugs of the present invention may also be delivered by the use of monoclonal antibodies as individual carriers to which the compound molecules are coupled. The prodrugs of the present invention may also be coupled with soluble polymers, such as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the prodrugs of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing about 0.01 to about 99.5%, more particularly, about 0.5 to about 90% of a drug-oligomer prodrug in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the drug-oligomer prodrug in a non-toxic liquid vehicle suitable for injection such as aqueous oleaginous medium and sterilizing the suspension or solution.

Alternatively, a measured amount of the drug-oligomer prodrug is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the drug-oligomer prodrug is admixed with low-melting water-soluble or insoluble solids such as polyethylene glycol, cocoa butter, higher ester as for example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the prodrugs according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

The prodrugs may also be administered orally to the patient in a suitable dosage form alone or together with an oral bioavailability-enhancing agent. Such bioavailablity-enhancing agent may be selected from the group consisting of cyclosporins A through Z, (Me-lle-4)-cyclosporin, dihydro cyclosporin A, dihydro cyclosporin C, acetyl cyclosporin A, genistein and related isoflavonoids, quercetin, calphostin, ceramides, morphine and morphine congeners. Preferred enhancing agents are cyclosporin A, cyclosporin C, cyclosporin D, cyclosporin F, dihydro cyclosporin A, dihydro cyclosporin C and acetyl cyclosporin A.

Further, the prodrugs of the present invention may be administered alone or with other chemotherapeutic agents (e.g., other anti-cancer agents), for example: amsacrine, anastrozole, asparaginase, asparaginase monohydrate, azelaic acid, *corynebacterium parvum*, dacarbazine, docetaxel, docetaxel anhydrous, erwinia asparaginase, etoposide, etoposide phosphate, formestane, gallium, gallium nitrate, mitotane, mitoxantrone, mitoxantrone Hcl, paclitaxel, paclitaxel semi-synthetic, pegasparagase, procarbazine, procarbazine Hcl, razoxane, tamoxifen, tamoxifen citrate, teniposide and topotecan. Preferred chemotherapeutic agents for use in combination therapy treatments with the prodrugs of the invention may be selected from the group consisting of: cisplatin, methotrexate, cytosine arabinoside and toposoimerase inhibitors. Where the prodrugs of the present invention are administered with other chemotherapeutic agents, the prodrugs and other chemotherapeutic agents may be administered simultaneously or sequentially. Additionally, where the drug component drug-oligomer prodrug of the present invention is an anti-cancer agent, such as etoposide, paclitaxel or docetaxel, the prodrug may be administered before, after or simultaneously with radiation therapy.

5. EXAMPLES

The construction of the prodrugs of the present invention involved the synthesis of an PEG-oligomer/polymer followed by conjugation to the drug. In the ensuing examples, etoposide is used as the drug; however, it will be appreciated that other drugs having suitable points of attachment (e.g., hydroxyl groups) for the PEG-oligomers/polymers of the present invention may be suitably employed. The applicants have also successfully employed this same general approach (i.e., conjugation of PEG-oligomers/polymers to hydroxyl groups of a therapeutic compound) using paclitaxel (data not shown).

Etoposide contains three reactive hydroxyl groups that can be used to conjugate oligomers (FIG. 1). The present invention permits derivatization of all three of these hydroxyl functions. The PEG-oligomer/polymer is attached to the hydroxyl groups on the etoposide molecule via a labile ester bond. The length of the amphiphilic component (e.g., PEG) can be varied to achieve the desired degree of amphiphilicity for the prodrug. The appendage of the PEG-oligomer/polymer not only imparts water solubility, but also behaves like a prodrug, hydrolyzing readily in vivo to release free etoposide.

5.1 Synthesis of PEG-Oligomer/Polymer-Drug Conjugates

5.1.1 Synthesis of Compound I [ClC(O)CH$_2$(OC$_2$H$_4$)$_2$OCH$_3$]

In the synthesis of Compound I, 6.2 ml (0.085 mol) of thionyl chloride was placed through a dropping funnel into a two-neck flask equipped with a reflux condenser. The flask was heated gently on a water bath and anhydrous [2-(2-Methoxy-ethoxy)-ethoxy]-acetic acid (10 g, 0.056 mol) was added during the course of 40 min. When all acid had been introduced, the reaction mixture was heated on a water bath for 30 min and reaction mixture was stirred overnight at room temperature. Excess thionyl chloride was removed by aspiration pump and the product was distilled under the reduced pressure. The product was characterized using IR and NMR.

5.1.2 Synthesis of Amphiphilic Compound II [ClC(O)CH$_2$OCH$_2$CH$_2$OCH$_3$]

Compound II was prepared using the same general steps as described above in Section 5.1.1 with regard to Compound I with the appropriate polyethylene glycol carboxylic acid starting material.

5.1.3 Synthesis of Amphiphilic Compound III [CH$_3$CH$_2$OC(O)(CH$_2$)$_2$O(CH$_2$CH$_2$O)$_2$CH$_2$CH$_3$]

In a round bottom flask NaH (3.9 g, 0.163 mol) was dispersed in 150 ml of anhydrous THF. Anhydrous di(ethylene glycol)ethyl ether (20 g, 0. 149 mol) was dissolved in THF (50 ml) and added dropwise to the NaH suspension. The reaction mixture was stirred for 2 hours. The solution of ethyl 3-bromopropionate (17.5 ml 0.140 mol) in THF (20ml) was added to a pre-cooled reaction mixture (t=–10°C.). The reaction mixture was stirred overnight, and the solvent was evaporated completely.

Ethylacetate was added to the residue and a mixture was washed with a solution of 10% NaCl and deionized water. The ethylacetate solution was dried over MgSO$_4$, filtered, and the solvent was evaporated. The residue was dried using a vacuum pump. The crude material was chromatographed on a silica gel column. Fractions containing the Compound III were collected, concentrated and characterized by TLC, HPLC, MS and NMR.

5.1.4 Hydrolysis of Compound III to Yield Compound IV

Compound III was stirred with 1N NaOH for 3–4 hours. The reaction mixture was concentrated to remove alcohol and acidified. A solution of NaCl was added and this was extracted with methylene chloride. The organic solution was washed with deionized water, dried over MgSO$_4$, filtered, and the solvent was evaporated to yield Compound IV [HOC(O)CH$_2$CH$_2$(OC$_2$H$_4$)$_2$OCH$_2$CH$_3$]. The product was characterized by TLC, IR and NMR.

5.1.5 Synthesis of Amphiphilic Compound V [ClC(O)CH$_2$CH$_2$(OC$_2$H$_4$)$_2$OCH$_2$CH$_3$]

Compound V was prepared using the same general steps as described above in Section 5.1.1 with regard to Compound III.

5.1.6 Conjugation of PEG-Oligomer/Polymer to Etoposide

In a round bottom 3 neck flask 0.250 g (0.4 mmol) of etoposide was dissolved in 4 ml of anhydrous chloroform. The solution was stirred under nitrogen atmosphere and 0.32 g (4 mmol) of pyridine was added. Then reaction mixture was cooled by ice bath and [2-(2-Methoxy-ethoxy)-ethoxy]-acetyl chloride was added dropwise. The reaction mixture was stirred for 3 hours then washed with 1% H$_2$SO$_4$ solution (2×10 ml) and deionized water, dried over MgSO$_4$, filtered and concentrated via rotovap.

The crude residue was chromatographed on a silica gel column, using chloroform-methanol 90–10% as a mobile phase. Fractions containing the product were collected, concentrated and dried via vacuum pump.

In initial tests of the etoposide conjugate synthesis scheme, the desired compound (FIG. 1) was isolated. The compound was characterized by 1H NMR, MS and HPLC analysis and shown to be the desired product. The solubility of this etoposide conjugate was found to be 7-fold greater man etoposide in phosphate buffer.

5.2 Cleavage of Conjugates in an Aqueous Environment

An example of the hydrolysis of the drug-oligomer conjugate in aqueous solution is set forth in FIG. 3. Samples of purified etoposide conjugate in phosphate buffers show increasing rate of hydrolysis as the pH increases. At pH 5.9 approximately 10% of the conjugate was hydrolyzed in 28 hours, while at pH 7.4 approximately 40% was hydrolyzed in the same time period. At pH 8.0 hydrolysis was essentially complete after 20 hours. No significant side products were observed during this conversion.

When the etoposide conjugate was incubated in fresh rat plasma at 37° C. hydrolysis of the conjugated etoposide and appearance of free etoposide showed reciprocal behavior (FIG. 4). This indicates that hydrolysis of the PEG-oligomer/polymer etoposide conjugate is complete and releases free etoposide. Since free etoposide is known to have anticancer therapeutic effects, as described more fully in Section 1, and since the prodrug created by the applicants is metabolized to active etoposide under normal physiological conditions, it is clear that the prodrug of the present invention is capable of delivering the active anti-cancer drug to a subject.

5.3 Accumulation of Conjugates in the CNS Following I.V. Administration

Conjugates of etoposide were administered I.V. to Sprague Dawley rats at 9 μmol/kg. Measurement of free etoposide in plasma (FIG. 5) at various time points demonstrated that peak plasma etoposide concentration was increased by 60% and the half-life was extended by approximately 50% in rats given the etoposide conjugate (curve I) versus rats given etoposide (curve II).

When the etoposide concentration in brain tissue was measured in these rats the data revealed that injection with the etoposide conjugate led to a 3-fold increase in accumulation of free etoposide in the brain parenchyma (FIG. 6). These data agree with other studies conducted by the present inventors demonstrating an increased penetration of the blood-brain barrier by conjugated peptide hormones (data not shown).

5.4 Confirmation that the Etoposide Conjugate Inhibits Topoisomerase II

Covalent modification of a drug molecule will frequently alter its activity. While it is not strictly necessary that the conjugates do not impede the activity of the parent compound, since the conjugates are hydrolyzed in vivo to provide the active parent compound, it is nevertheless important to assess the biological activity of the etoposide conjugate so that any change in the biological activity can be factored into interpretation of data from subsequent experiments.

The ability of the etoposide conjugate to inhibit topoisomerase II activity can be assessed using a DNA-unknotting assay (Isabella, Capranico et al. 1990). In this assay, topoisomerase II resolves high molecular weight, highly interwound phage P4 DNA into smaller DNA fragments. Briefly, highly knotted P4 DNA is prepared and incubated with high salt nuclear extracts from HeLa cells containing topoisomerase II as described (De Isabella, Capranico et al. 1990; Giaccone, Gazdar et al. 1992). Varying concentrations of etoposide conjugate or native etoposide can be added to the reactions. After a 30-minute incubation at 37° C., the reactions are terminated by addition of sodium dodecyl sulfate and proteinase K and the DNA fractionated by gel electrophoresis. High and low molecular weight DNA can be visualized by ethidium bromide staining.

5.5 Further Definition of the Biodistribution and Pharmacokinetics of the Etoposide Conjugate The focus of the present effort is to enable active etoposide to cross physiologic barriers that free etoposide penetrates poorly. Recently published studies indicate that the P-glycoprotein multidrug resistance molecule and related proteins may be a key component of the barrier to etoposide penetration in the brain parenchyma. The drug transport molecules may also be responsible for the erratic intestinal absorption of etoposide.

Protein Delivery's conjugation technology enables more effective distribution of the conjugated molecule across both of these barriers. The amount of the etoposide conjugate that reaches various tissues, including the brain parenchyma and tumor tissue implanted in the brain, following I.V. administration can be measured. It can then be determined whether oral dosing with the etoposide conjugate can also result in therapeutic levels of free etoposide in the above tissues.

A number of studies suggest that extended exposure to etoposide may improve its cell-killing ability. In vivo etoposide has a relatively short half-life, which in turn requires repeated administration and attendant medical support. A particularly useful aspect of the conjugation technology is that the rate of hydrolysis of the prodrug can be adjusted to extend the half-life of etoposide in plasma. This offers the possibility to more readily titrate maintenance doses of the conjugate and more easily maintain plasma levels of free etoposide in the therapeutic range.

Animals and the 9L glioma tumor model. Adult Fischer rats (5–6 weeks of age) can be used for these studies. Experimental gliomas can be induced in the rats by stereotactic injection of 20,000 9L glioblastoma cells (Asai, Shibui et al. 1990) from in vitro cultures into the right frontal lobe. After 14 days the animals can be used for experiments.

Biodistribution following I.V. administration. Fischer rats (approximately 250 g weight) can be administered etoposide (5 mg/ml in dimethyl sulfoxide/water) at a dose of 5 mg/kg or an equivalent molar mass of the etoposide conjugate in phosphate buffered saline and injected through the caudal vein. Rats can be sampled at 4 hours and 24 hours. Groups of six rats from each treatment group can be euthanized by pentobarbital overdose before plasma and tissue harvest.

Blood samples can be collected by cardiac puncture into heparinized syringes. The blood samples can be centrifuged and the plasma stored at −20° C. until analysis. Tissues (heart, lung, brain, kidney, liver, skeletal muscle and tumor) can be rapidly dissected, rinsed in cold phosphate buffered saline, then snap frozen in liquid nitrogen until further processing.

Biodistribution following oral administration. A similar experimental design can be followed as for the oral dosing except that the drugs can be administered by oral gavage using a 20 ga. gavage needle. Etoposide can be diluted to 5 mg/mL in saline for a dose volume of 100 μL; etoposide conjugates can be diluted to yield a similar molar mass dose in 100 μL. Tissues can be harvested at the same time points and process the same way.

Pharmacokinetics following oral and I.V. dosing. Tumor-bearing Fischer rats can be administered etoposide or an equivalent molar mass of the etoposide conjugate as described for the biodistribution studies except that two dose levels can be tested: 1 mg/kg and 5 mg/kg. Groups of six rats can be sampled at 5, 10, 15, 30 and 60 minutes, as well as 2 hours, 4 hours and 24 hours. The rats can be euthanized by phenobarbital overdose and blood samples can be collected by cardiac puncture into heparanized syringes. Cells in the blood samples can be pelleted by brief centrifugation and plasma stored at −20° C.

Analysis of etoposide in plasma and tissues. Plasma and tissue concentrations of etoposide can be measured by HPLC (Eiseman, Eddington et al. 1994). Samples of plasma can be mixed 1:2 with acetonitrile. The samples can then be acidified by addition of an equal volume of 0.02 M sodium acetate (pH 4) to prevent hydrolysis of etoposide conjugates in the sample. Tissues can be thawed and immediately homogenized in two volumes of saline. One volume of homogenate can be mixed with 2 volumes of acetonitrile, then acidified by addition of and equal volume of sodium acetate as above. Cell debris in all of the samples can be removed by brief centrifugation.

Data analysis. Etoposide concentration in each sample can be determined by calculating the ratio of the area under the etoposide peak to that of the internal control. The concentration in mg/ml can be determined by comparison to a previously constructed standard curve for the internal control. Data can be tabulated as the mean [etoposide] +/−SE.

Pharmacokinetic analysis. Drug concentration-plasma profiles can be analyzed by using R-strip software. The area under the plasma concentration-time curve can be calculated and extrapolated to infinity. Bioavailability following oral administration can be calculated using the formula %=(AUCoral/AUCi.v. )×100. The total body clearance can be calculated using the equation CLtb=Dose/AUC and the volume of distribution can be calculated from the formula Vd=CLtb/Kel. The half life of distribution and half life of elimination can be determined by extrapolation from the initial and secondary log linear portions of the plasma-time concentration curves.

5.6 Confirmation of Efficacy of the Etoposide Conjugate

Conjugation of etoposide to PEG-oligomers/polymers is expected to enable treatment of CNS tumors through parenteral administration and potentially by oral administration as well. The etoposide conjugate can be tested for its ability to extend the life expectancy of rats bearing 9L tumors intracranially.

Tumor models. The 9L cell line can be maintained in culture as recommended by the American Type Culture Collection. Tumors can be induced by stereotactic inoculation of cells into the right frontal lobe of Fischer rats as described above. Rats can be used 14 days after intracranial inoculation. Prior to treatment, rats can be pooled and randomized into treatment groups.

Treatment regimen. The treatment regimen can use the highest non-lethal dose of etoposide or the etoposide conjugate as determined from the toxicity experiments. Groups of 10 rats can be treated with each compound and 10 can serve as untreated controls. Rats can be weighed on the first day of treatment and every other day thereafter.

Rats can be treated on days 1, 3, 5 and 7. The dose of drug can be given orally and I.V. for the glioblastomas. Neurological signs including crouching, lethargy and paralysis can be the endpoint for rats bearing glioblastomas. Rats can be observed for neurological signs daily. If death occurs between observations this can be used as the endpoint.

Samples can be analyzed on a Waters Alliance 2690 system using a water/acetonitrile mobile phase on a C-18 column with U.V. detection at 230 nm. Concentrations of analyte can be determined by comparing the area under the curve on the HPLC trace to a standard curve. Tissue and plasma samples can be spiked with 25 (g/mL cephalomannine as an internal control to correct for extraction efficiency.

5.7 Determination of Optimum Dose of Conjugated Etoposide

The optimum dose of conjugated etoposide can be determined in animal models. Extensive preclinical efficacy testing can be performed using multiple tumor models, both for CNS tumors and non-CNS tumors.

5.8 Conclusions

It is expected that the above-described empirical procedures will confirm an increase in free or conjugated etoposide concentration in brain parenchyma of animals given the etoposide conjugate relative to controls given etoposide. It is further expected that this work will confirm a statistically significant effect on survival of tumor-bearing animals given the conjugate relative to untreated controls. Additionally, oral bioavailability will be significantly increased in animals given the conjugate relative to animals given etoposide.

6. REFERENCES

Throughout the specification various patent and non-patent references have been cited. The entire disclosure of each of these references is incorporated herein by reference, as is the entire disclosure of each of the following references:

Abe, T., S. Hasegawa, et al. (1994). "Possible involvement of multidrug-resistance-associated protein (MRP) gene expression in spontaneous drug resistance to vincristine, etoposide and adriamycin in human glioma cells." *Int J Cancer* 58(6): 860–4.

Adams et al. (1993). "Taxol: A History of Pharmaceutical Development and Current Pharmaceutical Concerns." *Journal of the National Cancer Institute Monographs* 15: 141–147.

Asai, A., S. Shibui, et al. (1990). "Cell Kinetics of Rat 9L Brain Tumors Determined by Double Labeling with Iodo- and Bromodeoxyuridine." *Neurosurgery* 73: 254–258.

Beauchesne, P., S. Bertrand, et al. (1998). "Etoposide Sensitivity of Readioresistant Human Glioma Cell Lines." *Cancer Chemotherapy and Pharmacology* 41: 93–97.

Beijnen et al. 1994. "Bioanalysis, Pharmacokinetic, and Pharmacodynamics of the Novel Anticancer Drug Etoposide (Taxol)." *Seminars in Oncology* 21(5) Suppl 8(October): 53–62.

Brown, G. A., J. P. McPherson, et al. (1995). "Relationship of DNA topoisomerase II alpha and beta expression to cytotoxicity of antineoplastic agents in human acute lymphoblastic leukemia cell lines." *Cancer Res* 55(1): 78–82.

Cancer Facts & Figures 1998, American Cancer Society. 1999.

Carney, D. N. (1991). "The pharmacology of intravenous and oral etoposide." *Cancer* 67(1 Suppl): 299–302.

Cavalli, F., R. W. Sonntag, et al. (1978). "VP-16–213 monotherapy for remission induction of small cell lung cancer: a randomized trial using three dosage schedules." *Cancer Treat Rep* 62(3): 473–5.

Chresta, C. M., J. R. W. Masters, et al. (1996). "Hypersensitivity of Human Testicular Tumors to Etoposide-induced Apoptosis Is Associated with Functional p53 and a High Bax:Bcl-2 Ratio." *Cancer Research* 56: 1834–1841.

De Isabella, P., G. Capranico, et al. (1990). "Evidence of DNA topoisomerase II-dependent mechanisms of multidrug resistance in P388 leukemia cells." *Mol Pharmacol* 37(1): 11–6.

Deutsch et al. (1989). "Synthesis of Congeners and Prodrugs. 3. [1] Water-Soluble Prodrugs of Taxol with Potent Antitumor Activity." *J Med Chem* 32(4): 788–792.

Donelli, M. G., M. Zucchetti, et al. (1992). "Do anticancer agents reach the tumor target in the human brain?" *Cancer Chemother Pharmacol* 30(4): 251–60.

Eiseman, J. L., N. D. Eddington, et al. (1994). "Plasma pharmacokinetics and tissue distribution of paclitaxel in CD2F1 mice." *Cancer Chemother Pharmacol* 34(6): 465–71.

Ekwuribe, N., et al., U.S. patent application Ser. No. 09/134,803, "Blood-Brain Barrier Therapeutics."

Giaccone, G., A. F. Gazdar, et al. (1992). "Multidrug sensitivity phenotype of human lung cancer cells associated with topoisomerase II expression." *Cancer Res* 52(7): 1666–74.

Greco, F. A., D. H. Johnson, et al. (1991). "Chronic oral etoposide." *Cancer* 67(1 Suppl): 303–9.

Greenwald et al. (1996). "Drug Delivery Systems: Water Soluble Taxol 2'-Poly(ethylene glycol)Ester Prodrugs-Design and in Vivo Effectiveness." *American Chemical Society* 39: 424–431.

Greenwald et al. (1995). "Highly Water Soluble Taxol Derivatives: 7-Polyethylene Glycol Carbonates and Carbonates." *J Org Chem* 60: 331–336.

Hande, K. R. (1998). "Etoposide: Four Decades of Development of a Topoisomerase II Inhibitor." *European Journal of Cancer* 34(10): 1514–1521.

Hande, K. R., M. G. Krozely, et al. (1993). "Bioavailability of low-dose oral etoposide." *J Clin Oncol* 11(2): 374–7.

Hande, K. R., P. J. Wedlund, et al. (1984). "Pharmacokinetics of high-dose etoposide (VP-16-213) administered to cancer patients." *Cancer Res* 44(1): 379–82.

International Patent Application No. WO 98/58927, entitled, "Soluble Prodrugs of Etoposide," issued 30 Dec. 1998.

Joel, S. (1996). "The Clinical Pharmacology of Etoposide: an Update." *Cancer Treatment Reviews* 22: 179–221.

Kasahara, K., Y. Fujiwara, et al. (1992). "Determinants of Response to the DNA Topoisomerase II inhibitors Doxorubicin and Etoposide in Human Lung Cancer Cell Lines." *Journal of the National Cancer Institute* 84(2): 113–117.

Kingston, (1991). "The Chemistry of Taxol." *Phamac Ther* 52: 1–34.

Kinston, (1994). "Taxol: the chemistry and structure-activity relationships of a novel anticancer agent." *TIBTECH* 12: 222–227.

Kiya, K., T. Uozumi, et al. (1992). "Penetration of Etoposide into Human Malignant Brain Tumors After Intravenous and Oral Administration." *Cancer Chemotherapy and Pharmacology* 29: 339–342.

Kohler et al. (1994). "Evaluation of New Drugs, Etoposide (Taxol)." *Pharmacotherapy* 14(1): 3–34.

Kroll et al. (1998). *Neurosurgery* 42(5): 1083.

Leu, B. L. and J. D. Huang (1995). "Inhibition of intestinal P-glycoprotein and effects on etoposide absorption." *Cancer Chemother Pharmacol* 35(5): 432–6.

Long, (1994). "Subspecialty Clinics: Oncology, Etoposide (Taxol): A Novel Anticancer Chemotherapeutic Drug." *Mayo Clin Proc* 69: 341–345.

Mayer, U., E. Wagenaar, et al. (1997). "Full blockade of intestinal P-glycoprotein and extensive inhibition of blood-brain barrier P-glycoprotein by oral treatment of mice with PSC833." *J Clin Invest* 100(10): 2430–6.

N. J. Preston, (1996). "Etoposide (Taxol®)- a guide to administration." *European Journal of Cancer Care* 5: 147–152.

Parekh et al. (1997). "The Transport and Binding of Taxol." *Gen Pharmac* 29(2): 167–172.

Paul Workman, (1993) "Pharmacokinetics and Cancer: Successes, Failures and Future Prospects." *Cancer Surveys Volume 17: Pharmacokinetics and Cancer Chemotherapy*: 1–27.

Rowinsky et al. (1993). "Taxol: Pharmacology, Metabolism and Clinical Implications." *Cancer Surveys, Vol. 17: Pharmacokinetics and Cancer Chemotherapy*: 283–305.

Rowinsky et al. (1992). "Taxol: The First of the Lipophilic drugs, an Important New Class of Antitumor Agents." *Seminars in Oncology* 19(6): 646–662.

Rowinsky et al. (1991). "The Clinical Pharmacology and Use of Antimicrotubule Agents in Cancer Chemotherapeutics." *Pharmac Ther* 52: 35–84.

S. B. Horwitz, (1994). "Taxol* (etoposide): Mechanisms of action." *Annals of Oncology* 5 (Suppl. 6): S3–S6.

S. G. Arbuck, (1994). "Taxol* (etoposide): Future directions**." *Annals of Oncology* 5 (Suppl. 6): S59–S62.

Schinkel, A. H., E. Wagenaar, et al. (1996). "P-glycoprotein in the blood-brain barrier of mice influences the brain penetration and pharmacological activity of many drugs." *J Clin Invest* 97(11): 2517–24.

Schinkel, A. H., J. J. Smit, et al. (1994). "Disruption of the mouse mdr 1a P-glycoprotein gene leads to a deficiency in the blood-brain barrier and to increased sensitivity to drugs." *Cell* 77(4): 491–502.

Slevin, M. L. (1991). "The clinical pharmacology of etoposide." *Cancer* 67(1 Suppl): 319–29.

Slevin, M. L., S. P. Joel, et al. (1989). "The effect of dose on the bioavailability of oral etoposide: confirmation of a clinically relevant observation." *Cancer Chemother Pharmacol* 24(5): 329–31.

Sparreboom, A., J. van Asperen, et al. (1997). "Limited oral bioavailability and active epithelial excretion of paclitaxel (Taxol) caused by P-glycoprotein in the intestine." *Proc Natl Acad Sci U S A* 94(5): 2031–5.

Straubinger et al. (1993). "Novel Taxol Formulations: Taxol-Containing Liposomes." *Journal of the National Cancer Institute Monographs* 15: 69–78.

Kroll, Robert A. Neurosurgery, Vol. 42, No. 5, May 1998.

U.S. patent application Ser. No. 09/134,803, entitled "Blood-Brain Barrier Therapeutics" filed on Aug. 14, 1998.

U.S. patent application Ser. No. 60/153,579, entitled "Drug-PEG conjugate s," filed on Sep. 13, 1999.

U.S. patent application Ser. No. 09/476,974, entitled "Taxane Prodrugs," co-filed with the present application on Dec. 31, 1999.

U.S. patent application Ser. No. 09/336,548, entitled "Amphiphilic Drug-Oligomer Conjugates with Hydrolyzable Lipophile Components and Methods for Making and Using the Same" filed on Jun. 19, 1999.

U.S. Pat. No. 5,407,683, entitled, "Pharmaceutical Solutions and Emulsions Containing Taxol" issued Apr. 18, 1995.

U.S. Pat. No. 5,422,364, entitled, "Water Soluble Taxol Derivatives," issued Jun. 6, 1995.

U.S. Pat. No. 5,439,686, entitled, "Methods for In Vivo Delivery of Substantially Water Insoluble Pharmacologically Active Agents and Compositions Useful Therefor," issued Aug. 8, 1995.

U.S. Pat. No. 5,484,809, entitled, "Prodrugs for Oral Administration Containing Taxol or Substituted Taxol Covalently Bound to a Phospholipid," issued Jan. 16, 1996.

U.S. Pat. No. 5,560,933, entitled, "Methods for In Vivo Delivery of Substantially Water Insoluble Pharmacologically Active Agents and Compositions Useful Therefor," issued Oct. 1, 1996.

U.S. Pat. No. 5,608,087, entitled, "Water Soluble Taxol Derivatives," issued Mar. 4, 1997.

U.S. Pat. No. 5,795,909, entitled, "DHA-pharmaceutical Conjugates of Taxabes," issued Aug. 18, 1998.

U.S. Pat. No. 5,817,840, entitled, "Water Soluble Taxol Derivatives," issued Oct. 6, 1998.

The invention claimed is:

1. A method of treating a mammalian subject having a disease condition selected from the group consisting of cancers, tumors, and malignancies, said method comprising administering to the subject of an effective disease treating amount of a prodrug comprising:

(a) at least one therapeutic compound selected from the group consisting of a therapeutic compound comprising etoposide and a therapeutic compound comprising an etoposide analog which retains some or all of the therapeutic activity of etoposide; and (b) one or more PEG polymers and/or oligomers, each joined to a bonding site on the therapeutic compound by a hydrolyzable bond, said PEG polymers and/or oligomers each:

(i) comprising a straight or branched PEG segment consisting of 1 to 25 polyethylene glycol units; and (ii) comprising a salt-forming moiety.

2. The method of claim 1 wherein the PEG oligomer has a number of PEG units selected from the group consisting of 1, 2, 3, 4, 5, 6, 7, 8, and 9.

3. The method of claim 1 wherein the therapeutic compound is derivatized by from 1 up to the maximum number of sites of attachment for the PEG oligomer(s).

4. The method of claim 1 wherein the prodrug is administered by a route of administration which comprises an oral route of administration.

5. The method of claim 1 wherein the prodrug is administered by a route of administration which comprises a parenteral route of administration.

6. The method of claim 1 wherein the disease condition comprises a condition selected from the group consisting of small cell lung cancer, non-small cell lung cancer, testicular cancer, lymphoma, leukemia, ovarian cancer, and gastric cancer.

7. The method of claim 1 wherein the prodrug is administered as a component of a pharmaceutical composition comprising:
(a) the prodrug; and
(b) a pharmaceutically acceptable carrier.

8. The method of claim 7 wherein the pharmaceutical composition is in a form suitable for oral administration.

9. The method of claim 7 wherein the pharmaceutical composition is in a form suitable for parenteral administration.

10. A method of treating a mammalian subject having a disease condition selected from the group consisting of cancers, tumors and malignancies, said method comprising administering to the subject of an effective disease treating amount of a prodrug comprising a therapeutic compound selected from the group consisting of a therapeutic compound comprising etoposide and a therapeutic compound comprising an etoposide analog which retains some or all of the therapeutic activity of etoposide and wherein the therapeutic compound is joined by hydrolyzable bond(s) to one or more PEG oligomer(s) selected from the group consisting of:

(Formula 2)

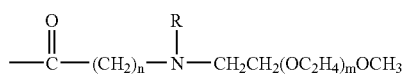

wherein n is from 1 to 7, m is from 2 to 25, and R is hydrogen or a lower alkyl;

(Formula 3)

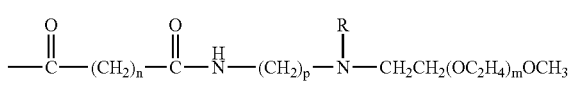

wherein n is from 1 to 6, p is from 2 to 8, m is from 2 to 25, and R is hydrogen or a lower alkyl;

(Formula 4)

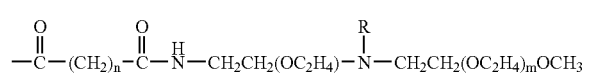

wherein n is from 1 to 6, m and r are each independently from 2 to 25, and R is hydrogen or a lower alkyl;

(Formula 5)

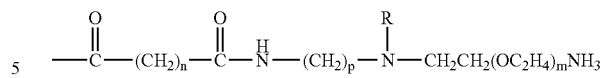

wherein n is from 1 to 6, p is from 2 to 8, m is from 2 to 25 and R is hydrogen or a lower alkyl;

(Formula 6)

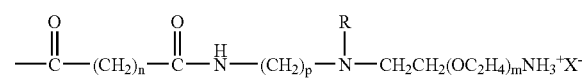

wherein n is from 1 to 6, p is from 2 to 8, m is from 2 to 25, $X^-$ is a negative ion and R is hydrogen or a lower alkyl;

(Formula 7)

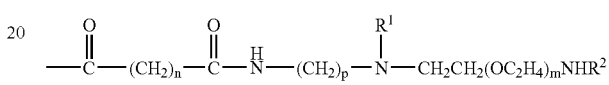

wherein n is from 1 to 6, p is from 2 to 8, m is from 2 to 25, and $R^1$ and $R^2$ are each independently hydrogen or a lower alkyl;

(Formula 8)

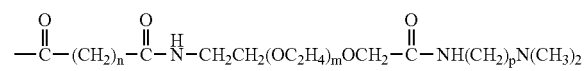

wherein n is from 1 to 6, p is from 2 to 8 and m is from 2 to 25;

(Formula 9)

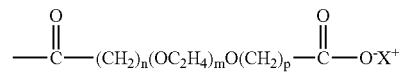

wherein n and p are each independently from 1 to 6, m is from 2 to 25 and $X^+$ is a positive ion;

(Formula 10)

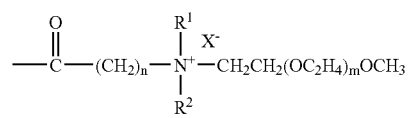

wherein n is from 1 to 5, m is from 2 to 25, and wherein $R^1$ and $R^2$ are each independently hydrogen or lower alkyl; and (Formula 11)

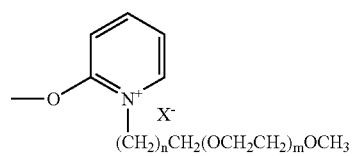

wherein n is from 1 to 6, m is from 2 to 25 and $X^-$ is a negative ion.

11. The method of claim 10 wherein the one or more PEG oligomer(s) each has 2, 3, 4 or 5 PEG units.

12. The method of claim 10 wherein the therapeutic compound is derivatized by from 1 up to the maximum number of sites of attachment for the PEG oligomer(s).

13. The method of claim 10 wherein the prodrug is delivered by a route of administration which comprises an oral route of administration.

14. The method of claim 10 wherein the prodrug is delivered by a route of administration which comprises an parenteral route of administration.

15. The method of claim 10 wherein the disease condition is selected from the group consisting of cancers, tumors and malignancies.

16. The method of claim 10 wherein the disease condition comprises a condition selected from the group consisting of small cell lung cancer, non-small cell lung cancer, testicular cancer, lymphoma, leukemia, ovarian cancer, and gastric cancer.

17. The method of claim 10 wherein the prodrug is administered as a component of a pharmaceutical composition comprising:
(a) the prodrug; and
(b) a pharmaceutically acceptable carrier.

18. The method of claim 17 wherein the pharmaceutical composition is formulated for oral administration.

19. The method of claim 17 wherein the pharmaceutical composition is formulated for parenteral administration.

20. The method of claim 10 wherein the PEG oligomer has a formula:

$$—\overset{O}{\underset{\|}{C}}—(CH_2)_n—\overset{R}{\underset{|}{N}}—CH_2CH_2(OC_2H_4)_mOCH_3 \quad \text{(Formula 2)}$$

wherein n is from 1 to 7, m is from 2 to 25, and R is hydrogen or a lower alkyl.

21. The method of claim 10 wherein the PEG oligomer has a formula:

$$—\overset{O}{\underset{\|}{C}}—(CH_2)_n—\overset{O}{\underset{\|}{C}}—\overset{H}{\underset{|}{N}}—(CH_2)_p—\overset{R}{\underset{|}{N}}—CH_2CH_2(OC_2H_4)_mOCH_3 \quad \text{(Formula 3)}$$

wherein n is from 1 to 6, p is from 2 to 8, m is from 2 to 25, and R is hydrogen or a lower alkyl.

22. The method of claim 10 wherein the PEG oligomer has a formula:

$$—\overset{O}{\underset{\|}{C}}—(CH_2)_n—\overset{O}{\underset{\|}{C}}—\overset{H}{\underset{|}{N}}—CH_2CH_2(OC_2H_4)_r—\overset{R}{\underset{|}{N}}—CH_2CH_2(OC_2H_4)_mOCH_3 \quad \text{(Formula 4)}$$

wherein n is from 1 to 6, m and r are each independently from 2 to 25, and R is hydrogen or a lower alkyl.

23. The method of claim 10 wherein the PEG oligomer has a formula:

$$—\overset{O}{\underset{\|}{C}}—(CH_2)_n—\overset{O}{\underset{\|}{C}}—\overset{H}{\underset{|}{N}}—(CH_2)_p—\overset{R}{\underset{|}{N}}—CH_2CH_2(OC_2H_4)_mNH_2 \quad \text{(Formula 5)}$$

wherein n is from 1 to 6, p is from 2 to 8, m is from 2 to 25 and R is hydrogen or a lower alkyl.

24. The method of claim 10 wherein the PEG oligomer has a formula:

$$—\overset{O}{\underset{\|}{C}}—(CH_2)_n—\overset{O}{\underset{\|}{C}}—\overset{H}{\underset{|}{N}}—(CH_2)_p—\overset{R}{\underset{|}{N}}—CH_2CH_2(OC_2H_4)_mNH_3^+X^- \quad \text{(Formula 6)}$$

wherein n is from 1 to 6, p is from 2 to 8, m is from 2 to 25, $X^-$ is a negative ion and R is hydrogen or a lower alkyl.

25. The method of claim 10 wherein the PEG oligomer has a formula:

$$—\overset{O}{\underset{\|}{C}}—(CH_2)_n—\overset{O}{\underset{\|}{C}}—\overset{H}{\underset{|}{N}}—(CH_2)_p—\overset{R^1}{\underset{|}{N}}—CH_2CH_2(OC_2H_4)_mNHR^2 \quad \text{(Formula 7)}$$

wherein n is from 1 to 6, p is from 2 to 8, m is from 2 to 25, and $R^1$ and $R^2$ are each independently hydrogen or a lower alkyl.

26. The method of claim 10 wherein the PEG oligomer has a formula:

$$—\overset{O}{\underset{\|}{C}}—(CH_2)_n—\overset{O}{\underset{\|}{C}}—\overset{H}{\underset{|}{N}}—CH_2CH_2(OC_2H_4)_mOCH_2—\overset{O}{\underset{\|}{C}}—NH(CH_2)_pN(CH_3)_2 \quad \text{(Formula 8)}$$

wherein n is from 1 to 6, p is from 2 to 8 and m is from 2 to 25.

27. The method of claim 10 wherein the PEG oligomer has a formula:

$$—\overset{O}{\underset{\|}{C}}—(CH_2)_n(OC_2H_4)_mO(CH_2)_p—\overset{O}{\underset{\|}{C}}—O^-X^+ \quad \text{(Formula 9)}$$

wherein n and p are each independently from 1 to 6, m is from 2 to 25 and $X^+$ is a positive ion.

28. The method of claim 10 wherein the PEG oligomer has a formula:

$$—\overset{O}{\underset{\|}{C}}—(CH_2)_n—\overset{R^1}{\underset{\underset{R^2}{|}}{\overset{|}{N^+}}}{\overset{X^-}{}}—CH_2CH_2(OC_2H_4)_mOCH_3 \quad \text{(Formula 10)}$$

wherein n is from 1 to 5, m is from 2 to 25, and wherein $R^1$ and $R^2$ are each independently hydrogen or lower alkyl.

29. The method of claim 10 wherein the PEG oligomer has a formula:

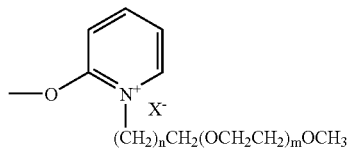

(Formula 11)

wherein n is from 1 to 6, m is from 2 to 25 and $X^-$ is a negative ion.

30. The method of claim 1 wherein the therapeutic compound is etoposide.

31. The method of claim 1 wherein the therapeutic compound is an etoposide analog which retains some or all of the therapeutic activity of etoposide.

32. The method of claim 10 wherein the therapeutic compound is etoposide.

33. The method of claim 10 wherein the therapeutic compound is an etoposide analog which retains some or all of the therapeutic activity of etoposide.

34. The method of claim 1 wherein the therapeutic compound is derivatized by 1 PEG oligomer.

* * * * *